US006864826B1

(12) United States Patent
Stove

(10) Patent No.: US 6,864,826 B1
(45) Date of Patent: Mar. 8, 2005

(54) RADAR APPARATUS FOR IMAGING AND/ OR SPECTROMETRIC ANALYSIS AND METHODS OF PERFORMING IMAGING AND/OR SPECTROMETRIC ANALYSIS OF A SUBSTANCE FOR DIMENSIONAL MEASUREMENT, IDENTIFICATION AND PRECISION RADAR MAPPING

(76) Inventor: George Colin Stove, 41 Craiglockhart Park, Edinburgh EH14 IEU (GB)

( * ) Notice: Subject to any disclaimer, the term of this patent is extended or adjusted under 35 U.S.C. 154(b) by 0 days.

(21) Appl. No.: 10/070,768

(22) PCT Filed: Sep. 7, 2000

(86) PCT No.: PCT/GB00/03431

§ 371 (c)(1),
(2), (4) Date: Mar. 7, 2002

(87) PCT Pub. No.: WO01/18533

PCT Pub. Date: Mar. 15, 2001

(30) Foreign Application Priority Data

Sep. 7, 1999 (GB) .............................................. 9921042

(51) Int. Cl.[7] .............................. G01S 7/40; G01S 13/00
(52) U.S. Cl. .............................. 342/22; 342/89; 342/90; 342/134; 342/165; 342/173; 342/175; 342/192; 342/195
(58) Field of Search .................... 342/82–103, 165–174, 342/1–12, 21, 22, 27, 28, 134, 135–144, 175, 176, 189, 190, 191–197, 25, 26; 383/719, 721, 733, 754–766, 772, 773–786, 871, 872, 873, 907, 908–916

(56) References Cited

U.S. PATENT DOCUMENTS 3,290,598 A * 12/1966 Thomas ......................... 342/4
3,427,533 A    2/1969 Gabillard 3,538,430 A    11/1970 Bulgakov
3,631,503 A * 12/1971 Tang et al. .................. 343/754
3,651,395 A     3/1972 Owen et al.

(List continued on next page.)

FOREIGN PATENT DOCUMENTS

GB       2316233        2/1998

OTHER PUBLICATIONS

Moschuring H. et al.: "The Measurement of Inhomogenities and of the Permittivity Distribution in MIC Substrates"; IEEE Instrumentation and Measurement Technology Conference, Boston, MA, USA, (Apr. 27–29, 1987).
Vlahacos C. P. et al.: "Quantitative Topographic Imaging Using a Near–Field Scanning Microwave Microscope"; Applied Physics Letters, U.S. American Institute of Physics (Apr. 6, 1998).

Primary Examiner—Bernarr E. Gregory
(74) Attorney, Agent, or Firm—Drinker Biddle & Reath LLP

(57) ABSTRACT

Radar apparatus and methods of use thereof for imaging and/or spectrometric analysis. The invention employs pulsed radar signals for magnifying, imaging, scale measuring, identifying and/or typecasting the composition of substances by radargrammetric imaging and/or statistical analysis of energy/frequency spectrums. The invention may be used to locate and/or distinguish a substance from other substances, to image a substance/feature and to monitor the movement of an imaged substance/feature. The systems and methods can be adapted for a variety of applications at a wide range of scales and distances, from large scale, long range applications such as geophysical imaging/analysis, to the small scale such as material typecasting applications and small scale (including microscopic) imaging/analysis, including biological and medical imaging and diagnostic applications. The invention includes novel antenna assemblies and novel data processing techniques.

61 Claims, 21 Drawing Sheets

U.S. PATENT DOCUMENTS

| | | |
|---|---|---|
| 3,690,164 A | 9/1972 | Gabillard et al. |
| 3,806,795 A | 4/1974 | Morey |
| 3,828,245 A | 8/1974 | Unterberger |
| 3,831,173 A | 8/1974 | Lerner |
| 4,218,678 A | 8/1980 | Fowler et al. |
| 4,308,499 A | 12/1981 | Thierbach et al. .......... 342/337 |
| 4,381,544 A | 4/1983 | Stamm |
| 4,504,833 A | 3/1985 | Fowler et al. |
| 4,511,842 A | 4/1985 | Moran et al. |
| 4,626,773 A | 12/1986 | Kroeger et al. |
| 4,698,634 A | 10/1987 | Alongi et al. ................. 342/22 |
| 4,746,867 A | 5/1988 | Gunton |
| 4,814,768 A * | 3/1989 | Chang ......................... 342/22 |
| 4,839,654 A | 6/1989 | Ito et al. ....................... 342/22 |
| 4,937,580 A | 6/1990 | Wills ........................... 342/22 |
| 5,192,952 A | 3/1993 | Johler ......................... 342/22 |
| 5,280,284 A | 1/1994 | Johler ......................... 342/22 |
| 5,392,056 A * | 2/1995 | DeTeso ...................... 343/873 |
| 5,420,589 A | 5/1995 | Wells et al. .................. 342/22 |
| 5,486,833 A | 1/1996 | Barrett ....................... 342/204 |
| 5,534,873 A * | 7/1996 | Weichman et al. .......... 342/165 |
| 5,543,799 A * | 8/1996 | Heger .......................... 342/22 |
| 5,561,431 A * | 10/1996 | Peele et al. .................. 342/192 |
| 5,565,872 A | 10/1996 | Prevatt et al. ............... 342/193 |
| 5,592,170 A | 1/1997 | Price et al. .................... 342/22 |
| 5,633,649 A | 5/1997 | Grossi et al. |
| 5,656,932 A | 8/1997 | Kitayoshi |
| 5,673,050 A | 9/1997 | Moussally et al. ............ 342/22 |
| 5,774,091 A | 6/1998 | McEwan ..................... 342/387 |
| 5,829,877 A | 11/1998 | Baath |
| 5,835,054 A | 11/1998 | Warhus et al. ................. 342/22 |
| 5,854,603 A * | 12/1998 | Heger .......................... 342/22 |
| 5,869,747 A | 2/1999 | Hulsman |
| 5,896,102 A * | 4/1999 | Heger .......................... 342/22 |
| 6,017,496 A | 1/2000 | Nova et al. |
| 6,037,908 A * | 3/2000 | Phillips et al. ............... 343/753 |
| 6,087,980 A | 7/2000 | Saryo ......................... 342/128 |
| 6,222,506 B1 * | 4/2001 | So .............................. 343/873 |
| 6,317,097 B1 * | 11/2001 | Smith ......................... 343/786 |
| 6,370,398 B1 * | 4/2002 | Kanamaluru et al. ....... 343/755 |

* cited by examiner

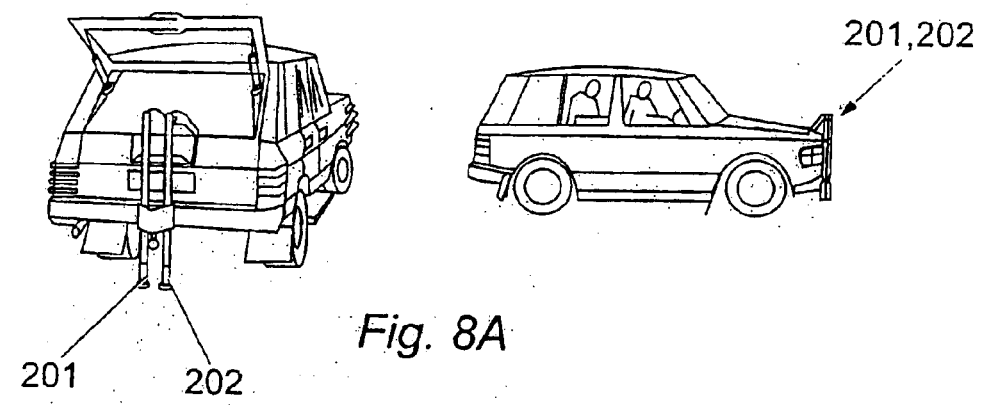
*Fig. 8A*
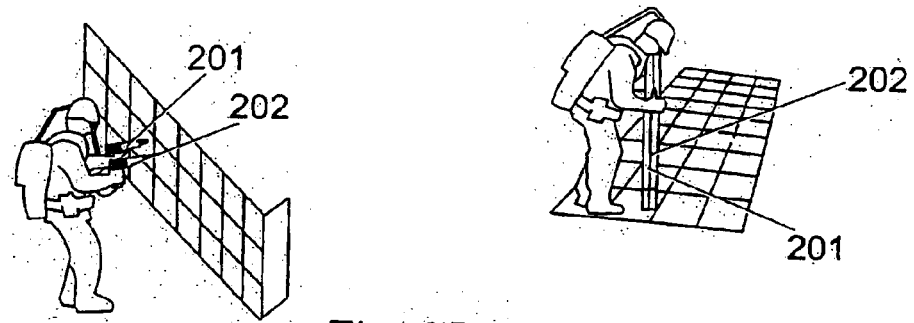
*Fig. 8B*
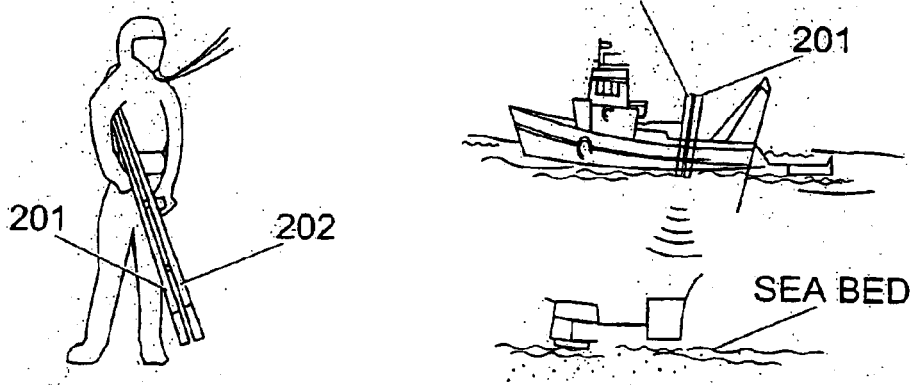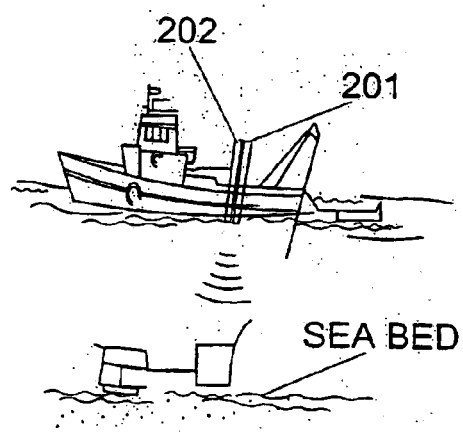
*Fig. 8C*  *Fig. 8D*

| MODE | Resolution Time (ps) | Resolution Space (m) (in salt water) | PRF (kHz) | Pw (ns) | TR (ns) | Fmax (MHz) | Fmin (MHz) | Ptr | ScanRate (traces/s) | 1/SR (Sdelay) | Ts (ns) |
|---|---|---|---|---|---|---|---|---|---|---|---|
| A1 | 50 | 0.00167 | 100 | 0.1 | 2 | 10000 | 1000 | 40 | 2500 | 0.0004 | 0.05 |
| A2 | 50 | 0.00167 | 100 | 0.1 | 5 | 10000 | 1000 | 100 | 1000 | 0.001 | 0.05 |
| A3 | 100 | 0.00167 | 100 | 0.1 | 10 | 5000 | 500 | 100 | 1000 | 0.001 | 0.1 |
| A4 | 250 | 0.00167 | 100 | 0.1 | 15 | 2000 | 200 | 60 | 1667 | 0.0006 | 0.25 |
| A5 | 500 | 0.00167 | 100 | 0.1 | 25 | 1000 | 100 | 50 | 2000 | 0.0005 | 0.5 |
| B1 | 250 | 0.01667 | 100 | 1 | 2000 | 2000 | 125 | 8000 | 12.5 | 0.08 | 0.25 |
| B2 | 500 | 0.01667 | 100 | 1 | 4000 | 1000 | 62.5 | 8000 | 12.5 | 0.08 | 0.5 |
| B3 | 625 | 0.01667 | 100 | 1 | 6000 | 800 | 50 | 9600 | 10.4 | 0.096 | 0.625 |
| B4 | 1250 | 0.01667 | 100 | 1 | 8000 | 400 | 25 | 6400 | 7.8125 | 0.128 | 1.25 |
| B5 | 2500 | 0.01667 | 50 | 1 | 10000 | 200 | 12.5 | 4000 | 6.25 | 0.16 | 2.5 |
| C1 | 2500 | 0.16667 | 50 | 10 | 20000 | 200 | 12.5 | 8000 | 0.625 | 1.6 | 2.5 |
| C2 | 5000 | 0.16667 | 25 | 10 | 40000 | 100 | 6.25 | 8000 | 0.3125 | 3.2 | 5 |
| C3 | 10000 | 0.16667 | 12.5 | 10 | 80000 | 50 | 2.25 | 8000 | 0.15625 | 6.4 | 10 |
| C4 | 40000 | 0.16667 | 6.25 | 10 | 160000 | 12.5 | 1 | 4000 | 0.15625 | 6.4 | 40 |
| C5 | 62500 | 0.16667 | 3.125 | 10 | 250000 | 12.5 | 1 | 40000 | 0.078125 | 12.8 | 40 |

Sampling Rate=Fs=2*Fmax
Range for all generic types=1/4Fmax-4 Fmax
Ptr=Time Range(TR)/Sampling Time (ts)
Sampling Time=Ts=1/2Fmax; time occupied
by 1 pixel in the y-direction going down the trace

*Fig. 12*

Ptr = number of pixels per trace
PRF = Pulse Repetition Frequency
Pw = Pulse Width
TR = Time Range
Fmax = Maximum Frequency
Fmin = Minimum Frequency
Resolution Time = time between pixels going down the trace
SR = Sampling Rate

RADAR APPARATUS FOR IMAGING AND/OR SPECTROMETRIC ANALYSIS AND METHODS OF PERFORMING IMAGING AND/OR SPECTROMETRIC ANALYSIS OF A SUBSTANCE FOR DIMENSIONAL MEASUREMENT, IDENTIFICATION AND PRECISION RADAR MAPPING

BACKGROUND OF THE INVENTION (1) Field of the Invention

This invention relates to radar apparatus and methods of use thereof for imaging and/or spectrometric a analysis. In particular, it relates to pulsed radar apparatus for magnifying, imaging, scale measuring, identifying and/or typecasting the composition of a substance by radargrammetric imaging and/or spectrometric analysis. The invention further relates to the use of the radar apparatus to locate and/or distinguish a substance from other substances. The invention may additionally be used to image a substance/feature and to monitor the movement of an imaged substance/feature. Such moving substances/features include but are not limited to the flow of blood and other substances moving within a human or animal body, and substances/features in a subterranean environment, such as the movement of water, oil, gas and/or contaminants below the ground surface, below standing or flowing water bodies, or below sea level and the seabed.

BRIEF SUMMARY OF THE INVENTION (2) Description of Related Art

Although ground penetrating radars (GPRs) are already known as non-destructive testing tools their analytical capabilities have been restricted and imaging is often crude using conventional devices. Conventional radar systems which use electromagnetic waves to investigate the internal structure of non-conducting substances within the ground provide relatively low resolution. Furthermore, they are often unwieldy devices and require skilled technical operators.

Radar systems and methods in accordance with the invention can be adapted for a variety of applications at a wide range of scales and distances. These vary from large scale, long range applications such as airborne, seaborne and ground based geophysical imaging/analysis of the Earth's surfaces and sub-surfaces, for example precision mapping and classification of sea-bed materials and also soil, sediment and rock type mapping and classification to medium scale, medium range applications such as "ground level" (on land or water bodies) imaging/analysis such as sea-bed and ground penetrating applications at relatively shallow depths, to the small scale such as material typecasting applications and small scale (including microscopic) imaging/analysis, including biological and medical imaging and diagnostic applications. The invention might also be extended to very long range/large scale space based imaging and analysis applications, such as orbital surveying of planets and astronomical applications.

The scale (i.e. range and resolution) the radar apparatus operates on is determined to a greater or lesser extent by the geometry of transmitting and receiving antenna apparatus employed in systems according to the invention. It is also affected by the properties of dielectric materials employed in such apparatus.

Certain aspects of the invention concern certain conditions being achieved during the set up of the apparatus so as to obtain "standing wave oscillations" in sample chambers and/or in antenna assemblies. In this respect it is important to selectively control the group velocity of the radiation as it is emitted or "launched" by the transmitter into the surrounding medium. In particular, for deep scanning it is important for the launch speed of the wave to be sufficiently slow to ensure that the wave can be accurately registered at a precise "zero time" location by the receiver after the pulse has been transmitted. The zero time position is the start position for range measurements and must be identified on the received radar signal to determine the true range represented by the received signal.

Setting up the standing wave oscillations for different time ranges or time windows such as, for example, 25 ns, 50 ns, 100 ns, 1000 ns or 20,000 ns, would all involve different zero time locations. Different time ranges are required to enable the different depth ranges required for certain precision mapping applications to be obtained. Accurate location of the zero time point is important and can be a difficult procedure: inaccurately pinpointing the zero time introduces a systematic shift in the location of all radar measurements. Certain embodiments of the invention register the zero time location prior to the received radar signal being converted from analogue to digital form. This enables a more accurate zero time to be located than can be obtained by using conventional techniques. Preferred embodiments of the invention locate the optimum position for time zero, for mapping or "staring" operations, by digital means using mathematical logic.

A blind spot of the order of 1 meter in close proximity (the near range) to the radar apparatus could generate an equivalent position shift in the radar map of features detected. Such near range blind spots can thus be highly undesirable. By accurately locating the position of the zero time point in the received signal radar, such blind spots can be mitigated or obviated.

The apparatus, systems and methods of the invention may be used for a variety of purposes, particularly but not exclusively three basic types of application. The first of these relates to identifying or "typecasting" unknown materials using their spectral characteristics; i.e. using energy-frequency characteristics, and may be referred to generally as "typecasting" operations. The second relates to use of the equipment in the field or laboratory, for detecting and/or mapping and/or measuring and/or analysing structures or materials, for example; these may be referred to generally as "surveying" operations. The third relates to use of the apparatus to locate materials previously typecast, and to search for them in the field or laboratory and may be referred generally to as the "searching" operations. The various types of operation are supported by suitable software which enables the field or laboratory imaging and analysis processes to be performed in near real time.

The inventor believes that a key feature of the invention is the set up of resonant conditions in the transmitter/receiver apparatus. This is affected by the dimensions and/or the geometry of a transmitter cavity and a receiver cavity which substantially surround respective transmitting and receiving antennae. In particular, the relative proportions of the lengths and widths of the antenna element(s) to the lengths and widths of the surrounding cavities are important. Ideally the internal diameter of an antenna cavity, whose walls may form the cathode element of an antenna in certain embodiments, is an integer multiple of the diameter of the internal antenna anode element, and similarly, the internal length of the is ideally an integer multiple of the length of the antenna anode element. The resonant conditions may be further affected by at least partially cladding the antennae element(s) with a suitable dielectric cladding material. Furthermore, the selection of a suitable dielectric material to clad the transmitting and receiving antenna elements is believed to further assist in the near range focusing and in more accurately pin-pointing the zero time position, the start position for range measurements.

The invention seeks to provide radar apparatus having a transmitter which is capable of emitting a beam of electromagnetic radiation into or towards a substance and a receiver which is capable of receiving electromagnetic radiation which has passed through or been reflected from the substance. The radiation is preferably a pulsed radar type signal. The radar signal may be provided by a conventional pulsed radar unit. The radar apparatus includes a suitable tuning means which is capable of controlling the spectral characteristics, for example the power and bandwidth, of the emitted radar signal. The spectral characteristics of the emitted radar signal are controlled so that by suitably irradiating a substance, a frequency response dependent on the composition of the substance can be detected by the receiver.

Suitable substances whose composition and/or structure can be detected by the apparatus include solids, liquids and composite substances such as powders, soil or sediment Liquid substances may be admixtures and/or emulsions (e.g. air/oil etc.).

The spectrometric analysis of the data acquired by the radar apparatus is performed on a computer which is capable of running a suitable software program to implement the required analysis.

The frequency response obtained by irradiating a substance displays characteristics which the inventor believes are at least partially dependent on the interaction of the transmitted signal with the subatomic structure of the substance to be analysed. The radar apparatus may further include suitable filter devices to control the spectral characteristics, for example bandwidth and/or polarisation, of the signals.

Optionally, the radar signal may be transmitted into a chamber capable of holding a sample of the substance.

In certain embodiments of the invention, the transmitted signal is controlled so that resonant conditions, i.e. standing waves, are set up within the radar apparatus. Preferably, the resonant conditions occur within transmitting/receiving cavities surrounding the antennae. Further resonant conditions may be generated within the substance and/or within a chamber enclosing the substance. Such resonant conditions may be established by selectively tuning the parameters of the emitted signal until the spectrum of the received signal indicates resonant conditions.

The radar apparatus is preferably configured so as to be capable of providing a highly collimated or selectively focussed beam over a desired range.

The boundary conditions for resonant standing waves are at least partially dependent on the surface boundaries of the substance itself, and may be further affected by any internal structure within the substance. Composite materials, for example, may exhibit more complex boundary conditions which can enable the structure of the substance to be determined; for example, the degree of granularity of a powdered sample may be determined to some extent using the radar apparatus.

The invention, in its various aspects, variants and optional and preferred features, is defined in the claims appended hereto.

BRIEF DESCRIPTION OF THE SEVERAL VIEWS OF THE DRAWINGS

Embodiments of the invention will now be described, by way of example only, with reference to the accompanying drawings in which:

FIGS. 8A to 8D are sketches which illustrate various embodiments of the invention suitable for the remote detection and/or imaging and/or typecasting of substances/ objects;

FIG. 12 is a table summarising various parameters as used in a variety of embodiments of the invention.

DETAILED DESCRIPTION OF THE INVENTION

Firstly, apparatus embodying various aspects of the invention will be described.

Figure 1:
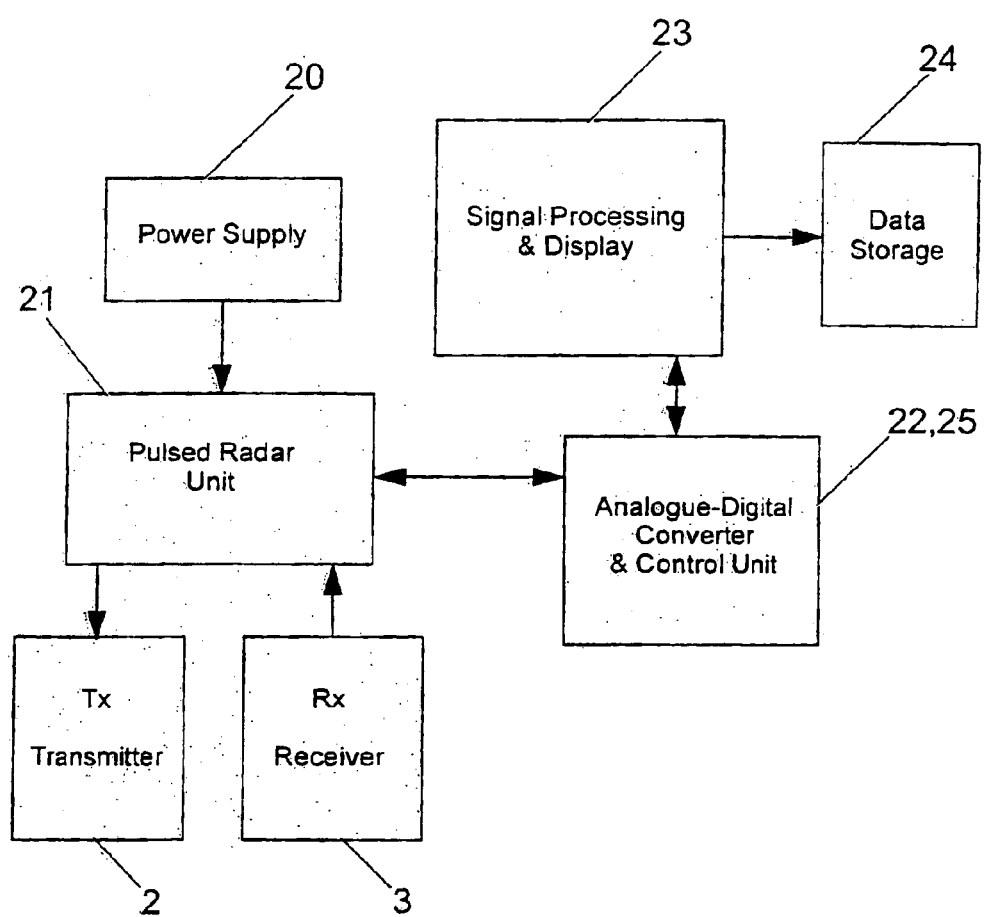
FIG. 1 is a block diagram of a radar system embodying one aspect of the present invention.

FIG. 1 is a generic block diagram illustrating the basic architecture of radar systems in accordance with the invention. A pulsed radar unit 21 is powered by a power supply 20. The radar unit 21 is connected to a transmitting ("Tx") antenna assembly or antenna array 2 and to a receiving ("Rx") antenna assembly or antenna array 3. The radar unit 21 may be of a conventional type, suitably a Ground Penetrating Radar (GPR) set, capable of providing controlled signal pulses to the Tx antenna assembly 2 and of receiving and processing return signals received by the Rx antenna assembly 3 and includes suitable input/output means to transmit and receive pulsed signals. The general configuration, controls etc. of radar sets of this type will be well known to persons skilled in the art and will not be described in detail herein. The controls of the radar unit 21 enable the characteristics of the transmitted pulse to be controlled, such characteristics including, for example, the pulse profile, width, duration and energy. For the purposes of the present invention, the radar set 21 acts primarily as a pulse generator for driving the Tx antenna.

The radar unit 21 is connected to an analog/digital (A/D) converter 22 and control unit 25, for controlling the operation of the radar unit 21 and for receiving analog signals received by the radar unit via the Rx antenna 3 and for converting the analog signals to digital form. The A/D converter and control unit 22,25 are in turn connected to signal processing and display means 23, typically comprising a suitably programmed personal computer, with associated data storage means 24 of any suitable type(s) (hard disk and/or tape and/or writable CD-ROM etc.). The computer 23 generally includes a suitable visual display device (not shown).

The power supply means 20 may be a mains supply, or a generator and/or a battery supply. The power supply means 20 may be provided internally within the pulse generation unit 21 or externally. Typically, the power supply means 20 is a 12 volt DC supply which may be a mains supply converted to 12V DC, or alternatively, especially in portable embodiments of the invention, be a 12V generator and/or a 12V DC battery supply.

The radar unit, A/D converter and control unit and the computer may be combined in a variety of configurations in custom built apparatus. As illustrated, the system preferably comprises a standard radar unit, a standard computer with software suited to the methods of the present invention, and a purpose built A/D converter and control unit.

The computer is suitably a ruggedised portable computer (laptop) with a suitably powerful processor, e.g. a Pentium-type processor, and adequate memory (RAM) and mass storage capacity.

The A/D converter 22 is preferably designed so that in use it is capable of receiving at least three signal inputs. An additional signal input, for example a voice data input, may also be provided.

The system is operable in at least one of three general modes of operation, in accordance with the invention: "chamber" modes in which a sample of material under investigation is enclosed in a chamber, the Tx antenna being arranged to irradiate the interior of the chamber and the Rx antenna being arranged to receive signals modified by the interaction of the transmitted signals with the chamber and its contents; "transillumination" modes in which the Tx antenna is arranged to transmit signals through a sample of material or an object, body or structure etc. under investigation and the Rx antenna is arranged to receive signals which have passed through the sample, object etc.; and "reflection" mode in which the Rx antenna receives signals transmitted by the Tx antenna and reflected by a sample, object, body or structure etc. These various modes of operation will be discussed in more detail below. The various modes of operation are used for a variety of imaging, mapping, measuring and typecasting functions, as shall also be described in more detail hereinafter.

Figure 2:
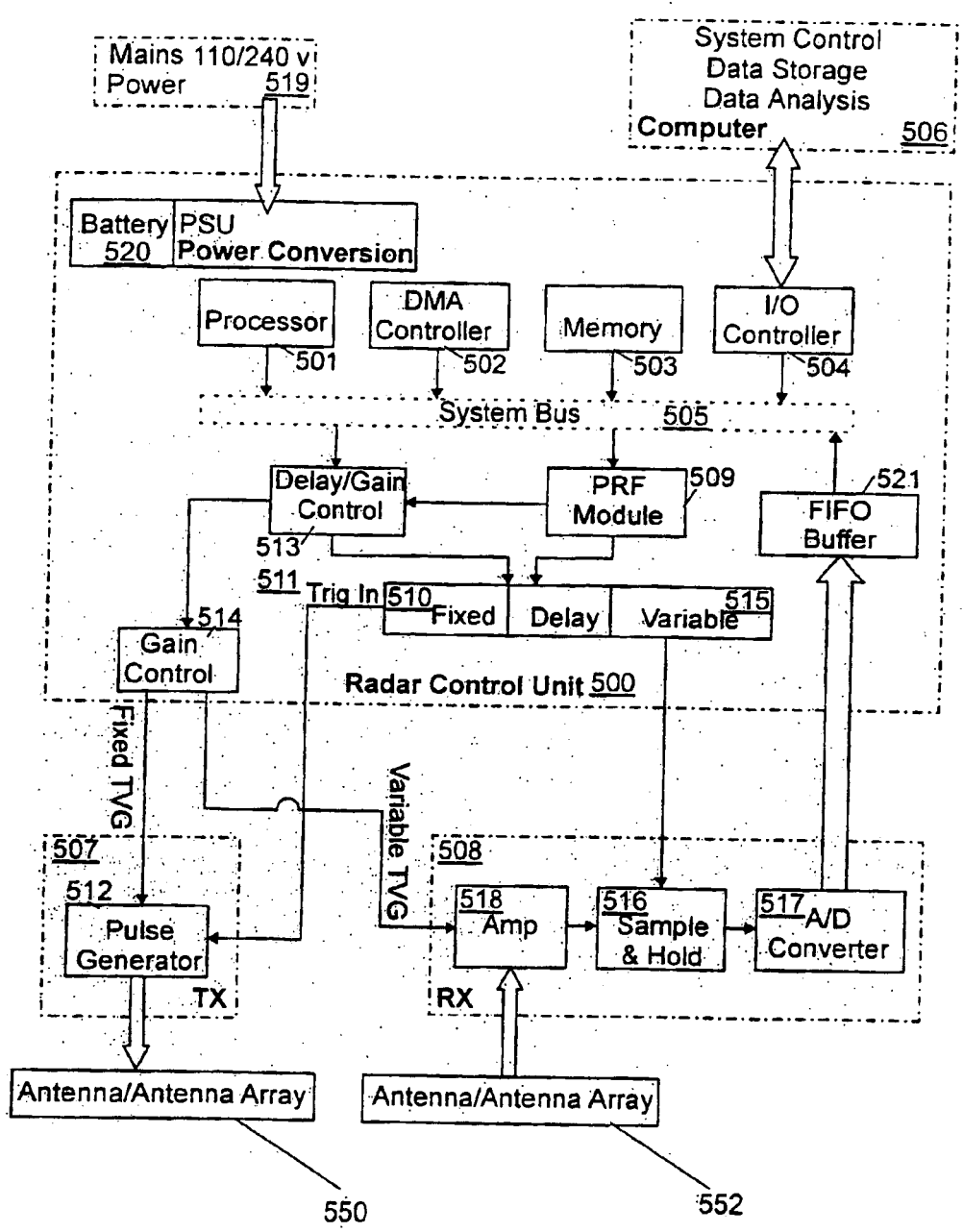
FIG. 2 is a block diagram of a preferred embodiment of a radar system similar to that of FIG. 1.

FIG. 2 illustrates a preferred embodiment of a multipurpose radar system in accordance with the invention which can employ a variety of types of transmitting and receiving antennas, antenna assemblies or antenna arrays, including the preferred antennas and antenna assemblies described hereinbelow.

Referring to FIG. 2, the system comprises a radar control unit (RCU) 500, a computer 506, a transmitter unit 507, a receiving unit 508, a transmitting antenna 550, a receiving antenna 552 and a power supply 519.

The RCU has its own motherboard with a processor 501, DMA controller 502, a buffer memory module 503 and an input/output controller 504, all linked to a system bus 505. The I/O controller 504 is directly connected to the external computer 506, which controls all digital set-ups, data storage and data analysis. The RCU 500 provides the timing signals for controlling the transmitting and receiving units 507 and 508, which are directly linked to the transmitting and receiving antennas 550, 552. The antennas 550, 552 may be single or multiple elements. The timing signals are controlled by parameters output from the computer 506 to the RCU 500. The RCU 500 also relays digitised data from the receiver unit 508 back to the computer 506. The RCU 500 consists of analogue and digital logic with a programmable central processing unit (CPU) 501.

The RCU sets up a Pulse Repetition Frequency (PRF). The transmitter unit 507 essentially consists of a pulse generator 512 designed to produce strong pulses with characteristics, including the PRF, determined by the RCU. The pulse is limited by the high voltage, current and power required. Extending the pulse width reduces the voltage and current needed for the same average pulse energy. Too short a pulse will produce too much high frequency energy which is not necessary for certain applications in which high frequencies are absorbed more than the lower frequencies in the subject under examination (e.g. the ground in sub-surface ground applications). Higher frequencies may be required for other applications including shallow range modes of operation (e.g. for microscopic slide scanning applications in medical tissue studies).

In the transmitter unit 507, the pulse is triggered by a digital "Trig in" pulse sent from the RCU 500, via a PRF module 509 which channels the Trig in pulse through a fixed delay line 510. The Trig in pulse 511 is responsible for triggering the transmitted pulse in the transmitter unit 507. A delay/gain control 513 in the RCU 500 controls a gain control 514 to generate a fixed time varying gain (TVG) and fixed delay line 510 for the transmitter unit 507. The same delay/gain control 513 operated upon by the PRF module 509 also creates a variable TVG for the receiver unit amplifier 518 and a variable delay line 515 for a sample and hold module 516 of the receiver unit 508. The rate at which pulses are transmitted is referred to as the pulse repetition frequency (PRF) and the PRF module 509 sets the required PRF for each particular mode of operation of the system. The PRF must be long enough to allow analogue to digital (A/D) conversion to be performed by the A/D converter 517 of the receiver unit 508 and to cover the required time window for the particular instrument measuring application.

The receiver unit 508 includes a low noise amplifier 518 which amplifies the analogue signal received via the receiver antenna 552, which is sampled by the sample and hold module 516 and digitised by the A/D converter 517 when requested by a digital signal from the RCU 500.

The A/D converter 517 is responsible for analogue to digital sampling and the digital sampling frequency should ideally be no greater than the time spacing between picture elements (pixels) of the output signal data. A smaller sampling interval results in aliasing (i.e. increasing noise) of the signal. A longer sampling interval attenuates the higher frequency components of the signal. The advantage of the variable TVG from the gain control 514 to the receiver amplifier is that the A/D conversion may be performed to the same precision with a lower number of bits.

The digital data obtained from the A/D converter enable real-time analysis of i) a positioning fix sign or chainage mark, enabling the location of a substance/image to be determined;

ii) imaging signal information;

iii) typecasting information—i.e. the spectral characteristics of the scanned substance/object;

iv) a voice-over to be further recorded from the user via a suitable microphone as a digital signal.

In use of the radar apparatus, the A/D converter converts the received signal from analogue format to a 12-bit digital signal and combines this with a synch pulse and electronic fix data. The signal is buffered and synchronised with a 16 bit computer signal to condition the data. Image data are converted into 8-bit image files.

The computer 506 controls the overall functions of the other units and provides a user interface for the selection of control and survey parameters, data collection, data enhancement, image production, image analysis, material typecasting, material testing and data logging etc.

The entire radar system is powered either by mains power 519 or battery power conversion 520.

There are four primary signal, data and control linkages between the components of the system: transmitter 507 to receiver 508, RCU 500 to transmitter 507, receiver 508 to RCU 500, and RCU 500 to computer 506. The transmitter to receiver linkage is via the antennas 550, 552 and intervening media such as air or other gases, water or other liquids, the ground, vacuum etc. There may also be unintentional transmitter-receiver linkage through RCU-transmitter cables and receiver-RCU cables if they are conducting. When this occurs, touching the cables may cause an electrical short which can affect output data. The RCU-transmitter and receiver-RCU linkages will generally be metal or glass fibre, but can be wireless connections such as radio or optical through vacuum and/or gaseous and/or liquid media. Metal is preferably avoided for the above mentioned reasons. The RCU-computer linkage will normally be a serial or parallel port connection, since the required data rates are not unusually high.

Other possible links include USB, PCMCIA, IrD or radio modem.

Examples of various antennas and antenna assemblies, embodying further aspects of the invention, will now be described, which are particularly suited for the purposes of the invention when operated in one or more of its various modes.

Figure 3A:
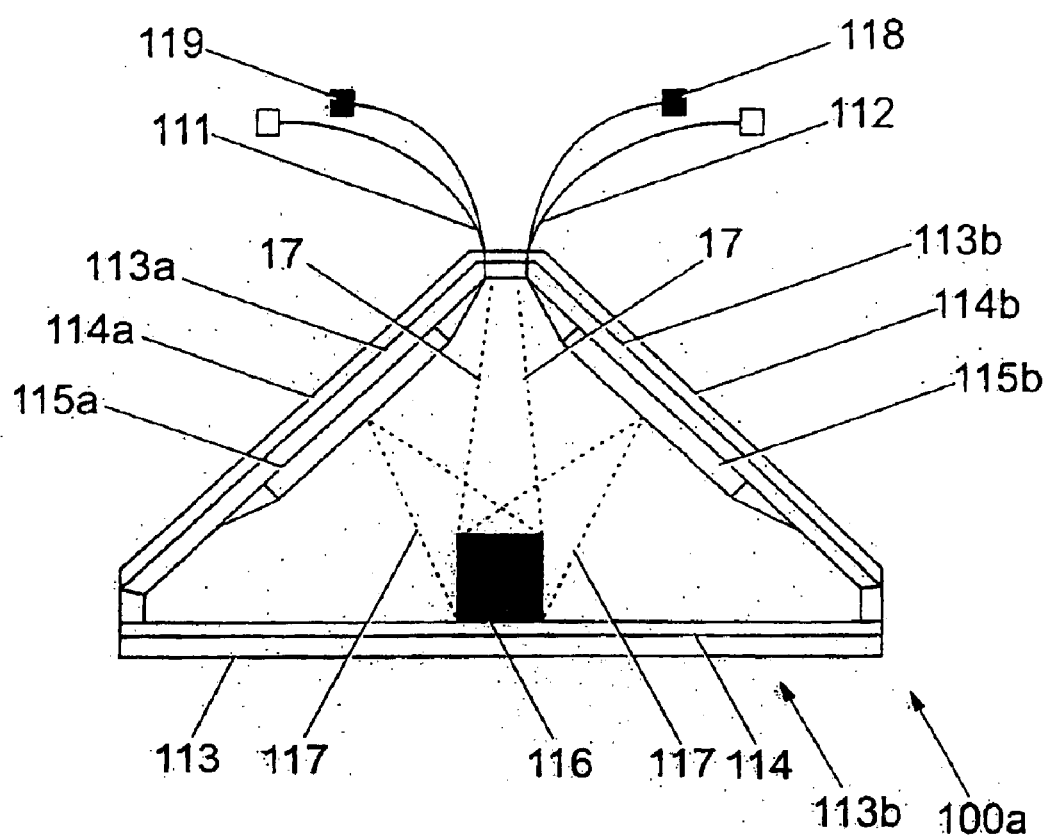
FIGS. 3A and 3B are cross-sections of test chambers incorporating receiving and transmitting antennas embodying another aspect of the invention.
Figure 3B:
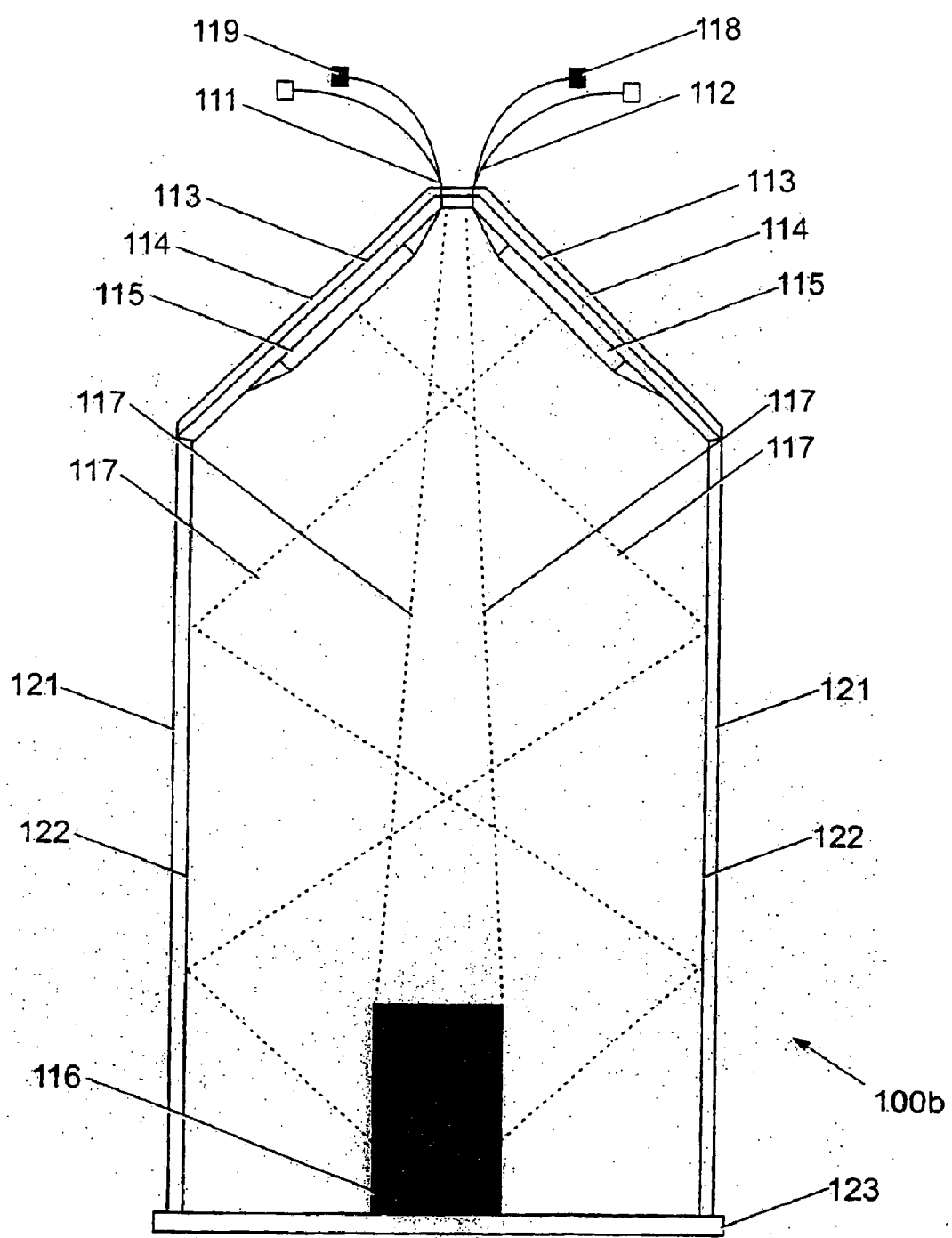
Figure 4:
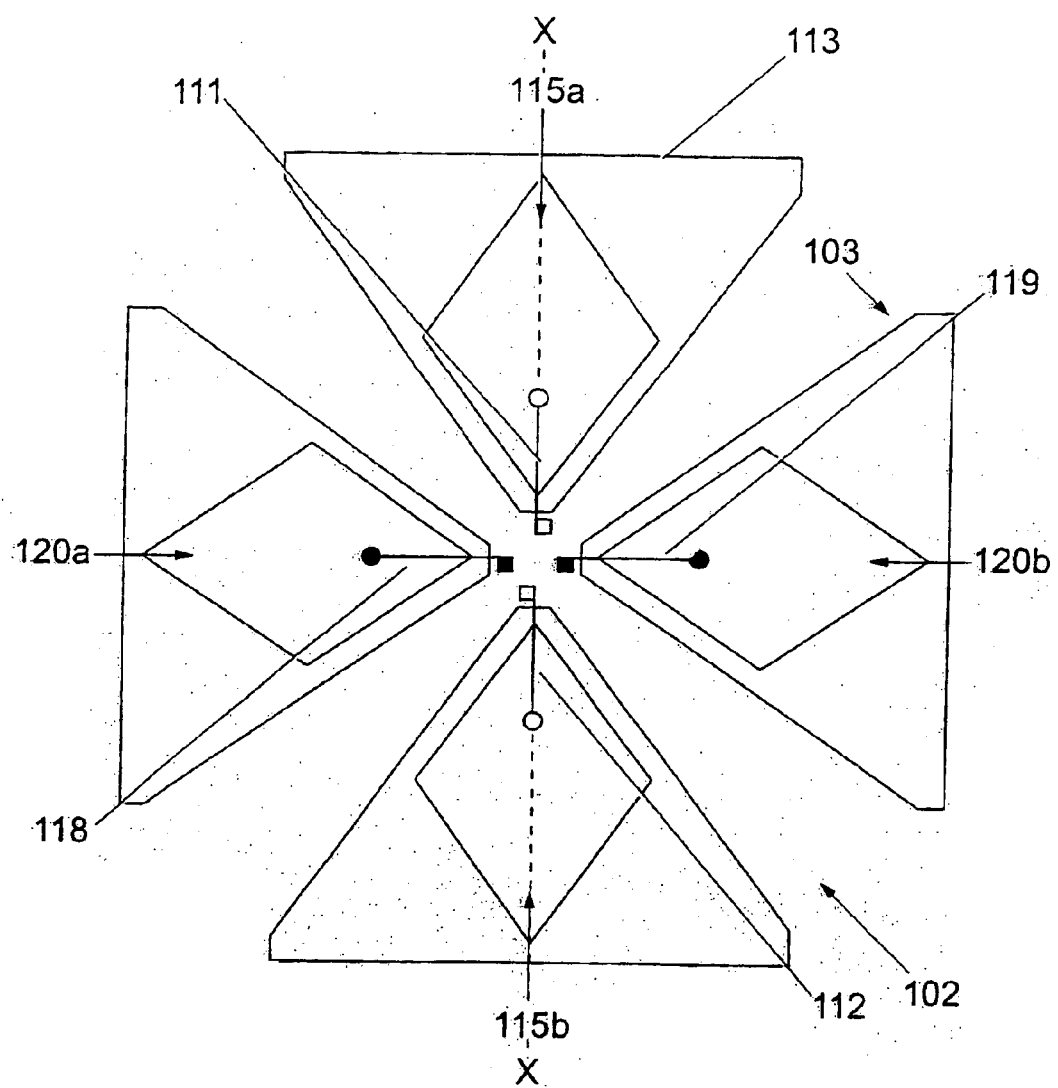
FIG. 4 is an exploded internal plan-view of the test chamber illustrated in FIG. 3A.

FIGS. 3A, 3B and 4 illustrate examples of antenna/chamber assemblies suited for chamber mode operations in accordance with the invention, particularly for typecasting applications performed on material samples or relatively small objects.

FIG. 3A shows a cross-section through a sample irradiation chamber 100a which has a preferred pyramidal geometry FIG. 3B shows a cross-section through a sample irradiation chamber 100b which has an upper section with a pyramidal geometry similar to that of FIG. 3A but with a rectangular chamber extending downwardly from the base of the pyramid. FIG. 4 shows an exploded overhead view of the embodiments illustrated in FIGS. 3A and 3B indicating the antenna configuration.

The cross-section along lines X–X' of FIG. 4 is illustrated in FIG. 3A. In FIG. 4. A transmitting antenna 102 and a receiving antenna 103 are directly provided within the chambers 100. FIG. 3A shows the configuration of the transmitting antenna 102 in profile. A cathode feed connector wire 111 connects a cathode half of a transmitting bowtie dipole element 115a to the pulse generator of the system. An anode feed connector wire 112 connects the anode half of the transmitter bowtie element 115b provided on the opposite internal face of the chamber 100 to the receiver side of the system.

FIG. 4 illustrates the orientation of a receiving cathode bowtie dipole component 120a and connecting cathode feed connector wire 118 and a receiving anode bowtie dipole component 120b and connecting anode feed connector wire 119.

To increase the detection of cross-polarised reflections and to reduce the detection of other reflections, the receiver dipole components 120a, 120b are orientated at 900 to the transmitter dipole components 115a, 115b.

To ensure that a sample of material 116 placed within the chamber 100 (as FIG. 3A and 3B show) is sufficiently irradiated, the chamber 100 is provided with a suitable geometry to enhance the internal reflection and is suitably sealed to eliminate radiation leaks. Alternatively the chamber and/or transmitter/receiver tubes are vacuum sealed. A wall 113a or base 113b of the chamber 100 is configured so that access to the interior is provided so as to enable the sample 116 to be placed inside. For example, the entire base 113b of the chamber 100 may be detachable.

Radiation shielding of the interior and the elimination of any radiation leaks from the interior is provided by the selection of suitable construction materials for the chamber 100. For example, the walls 113a and base 113b of the chamber 100 may be constructed from an insulating material such as plastic, and may be bonded externally or internally to an electrically conducting material such as copper 114. Alternatively, the base 113b may be made of a metallic substance to optimise base reflections.

In the FIG. 3B chamber, to ensure that the optimal number of reflections occur in the chamber interior, the rectangular side walls 122 are preferably provided with a metallic inside surface. This enables omnidirectional backwall and base reflections from the transmitted radiation to penetrate the sample. The geometry of the chamber 100 is preferably selected to maximise the irradiation of the sample. As FIGS. 3A and 3B show, the primary direction of the radiation pattern is orientated to and from the walls 113, base 123 and the sample 116.

FIGS. 5A to 5D are cross-sectional side views of preferred embodiments of antenna assemblies in accordance with one aspect of the invention which can be deployed as receivers and/or transmitters in various systems and methods embodying the invention. These embodiments are applicable to all of the various operational modes and functions in accordance with the various aspects of the inventions i.e. chamber, transillumination and reflection modes and imaging/mapping and typecasting functions. The configuration of the antenna assemblies is scalable over a wide range of dimensions for different applications.

At the front end 203 of the assembly, a focusing system is provided by a suitable lens device 204, for example of the type of a Fresnel Zone Plate (FZP) lens. The FZP lens comprises two concentric slit-ring apertures 224, 225 separated by a ring spacer 226, for example a metallic (e.g. polished brass) front-end internal reflecting ring. The main body of the assembly consists of a tube 227, preferably having a reflective metallic composition, for example polished brass or stainless steel. A back wall reflector 232 is provided in the form of a concave metallic ring (again polished brass or any other suitably reflective material may be used) which is bonded to the tube 227 and to a cathode connector 233. Through the centre of the backwall reflector 232 protrudes an anode element 230, which is preferably a narrow hollow tube element, for example comprising copper, and which is separated from the grounded cathode walls of the assembly by insulating material 231.

The diameter $D_A$ of the anode element 230 is preferably an exact multiple of the internal diameter $D_T$ of the tube 227. The un-insulated portion of the anode element 230 also protrudes into the interior of the tube 227 by a distance $L_A$ which is preferably an exact multiple of the total reflecting distance $L_T$ from the back wall reflector 232 to the front wall reflecting ring 226.

For example, an anode width of 2 mm and a tube inner diameter of 10 mm gives a ratio $D_A:D_T$ of 1:5. Ideally, the ratios between the anode diameter and the tube diameter are integers and similarly the ratios between the anode length and the tube length are integers. In this case, an anode length $L_A$ of 19.05 mm and a tube inner length $L_T$ of 190.5 mm between the back wall internal reflector 232 and front wall internal reflector 226 gives a longitudinal standing wave ratio parameter of $L_A:L_R$ of 1:10. This balances the lateral ratio parameter $D_A:D_T$ of 1:5 to achieve optimum standing wave resonance in the tube, before the wave is launched through the aperture.

These proportions are selected to optimise resonant reflection conditions in the assembly. The resonant amplification effect and the propagation of signals through the assembly is further optimised by the appropriate selection of a dielectric cladding material 228 which substantially fills the interior of the tube 227 (and, preferably, the interior of the tube forming the anode 230, in order to maximise the effective dielectric constant of the assembly for a given dielectric material). The cladding material 228 preferably has a high dielectric constant to provide an optimum resonant amplification through the antenna assembly. The dielectric material may be a liquid or a solid or a mixture thereof. Preferably, the dielectric material comprises a powdered solid packed within the interior of the tube 227.

An anode feed wire connects the anode element connector 236 to a highly resistive (e.g. 75 Ω) lead cable 235. The back reflector 232 is grounded by connecting a ground wire from the lead cable 235 to the cathode element connector 237.

The configuration of the assembly is such that the transmitted energy radiated from the anode 230 is highly collimated within the body of the assembly. When the assembly is used as a transmitter the concentric focussing ring slits 224, 225 at the transmitting end have the effect of focussing the collimated beam exiting the assembly at a predetermined distance from the exit aperture. Depending on the configuration of the focussing ring slits, and/or the use of additional focussing elements such as dielectric lens attachments described below, the characteristics of the transmitted beam can be modified so that the focal distance of the assembly may be varied over a wide range, effectively from the exit aperture to infinity, for different applications.

Figure 5A:
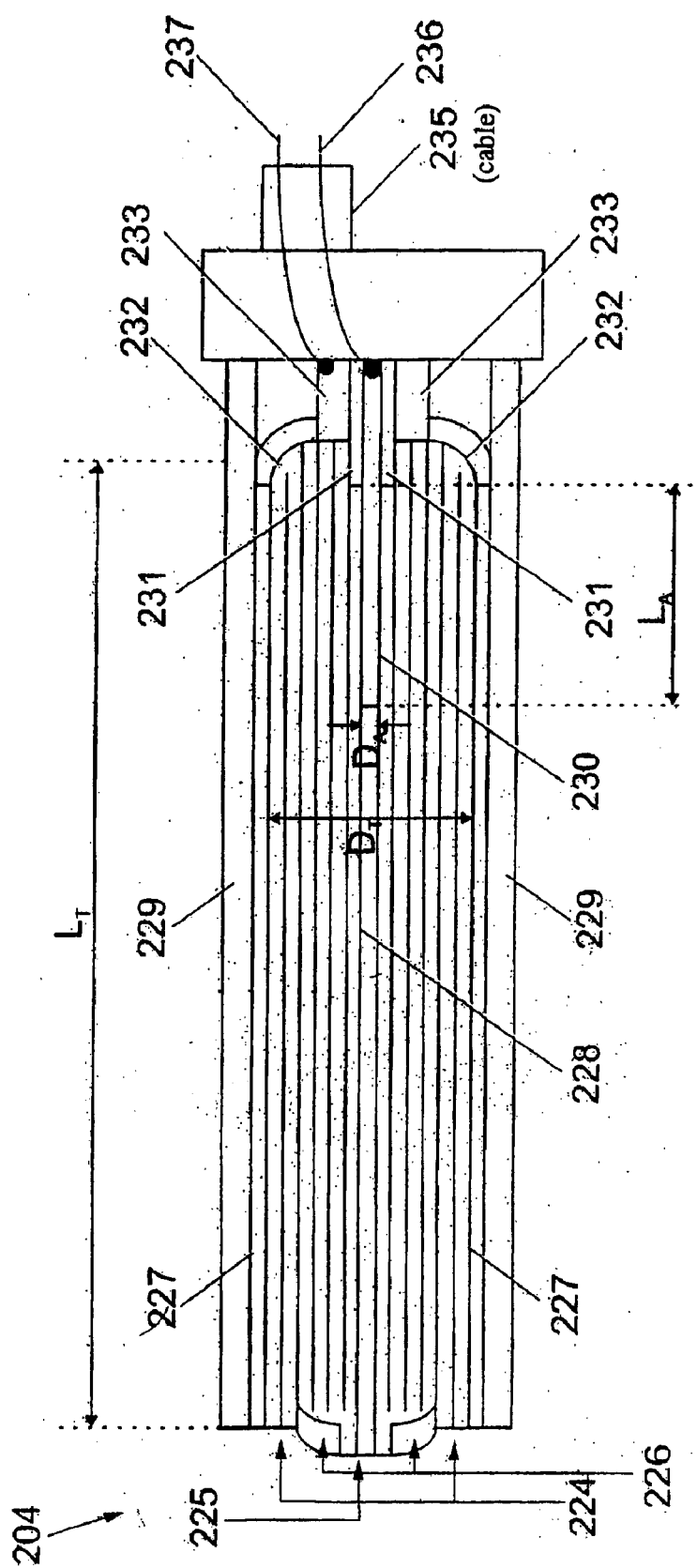
FIG. 5A is a cross-sectional side view of an antenna assembly for use as a transmitter or receiver embodying a further aspect of the invention.
Figure 5B:
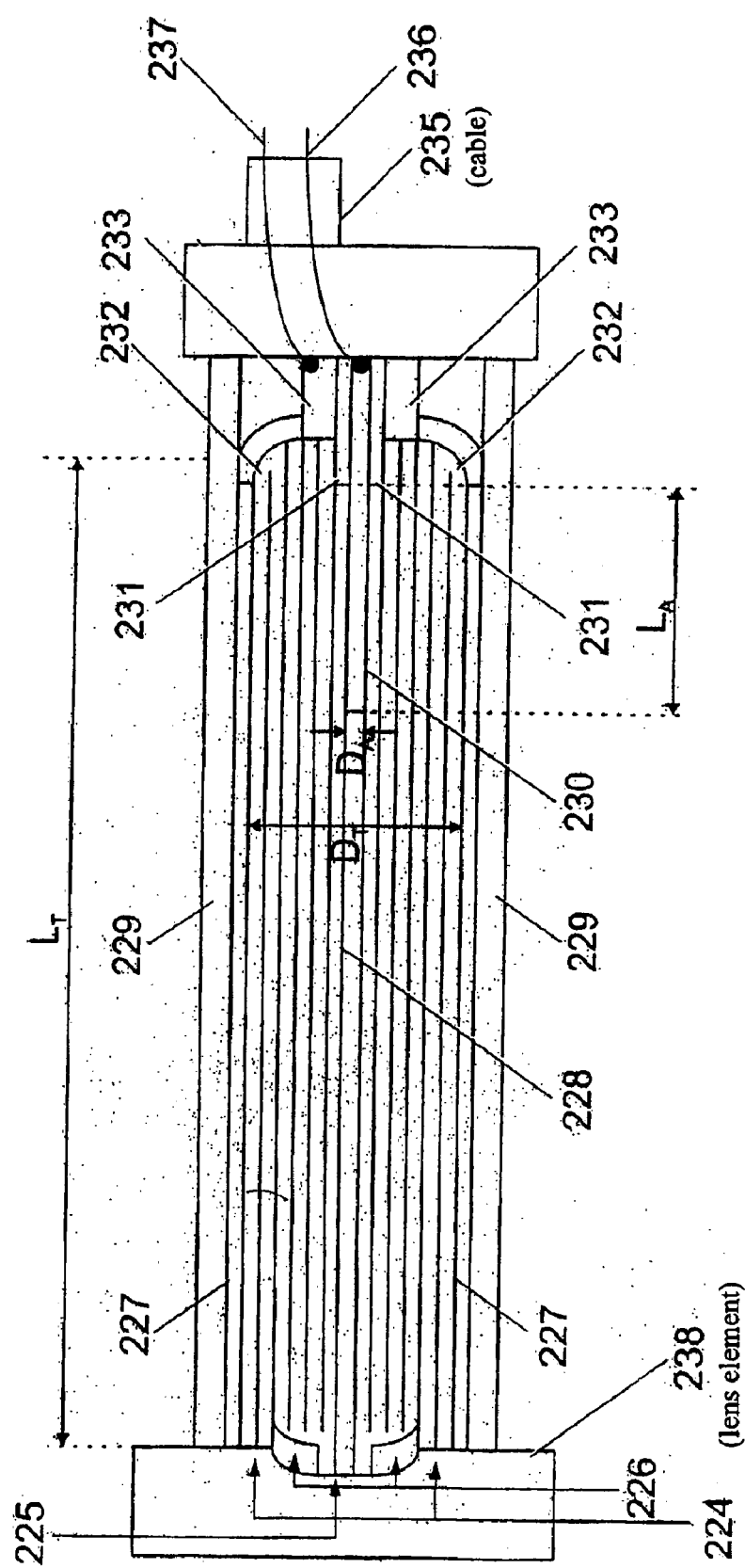
FIG. 5B is a cross-sectional side view of a first variant of the antenna assembly of FIG. 5A.

FIG. 5B shows an antenna assembly similar to that of FIG. 5A, which further includes a cylindrical dielectric lens element 238 with planar end surfaces. This type of lens attachment modifies the beam leaving the assembly in a manner which depends on the distance of the outer end surface of lens attachment relative to the inherent focal distance of the main assembly, and on the refractive index and dielectric properties of the lens attachment relative to those of the dielectric cladding material inside the assembly and relative to those of the external medium/media into which the bean is transmitted from the device. This embodiment is particularly useful when the lens surface is located at the inherent focal distance of the assembly and placed in contact with a surface under examination, acting as a spacer element for precise focussing.

Figure 5C:
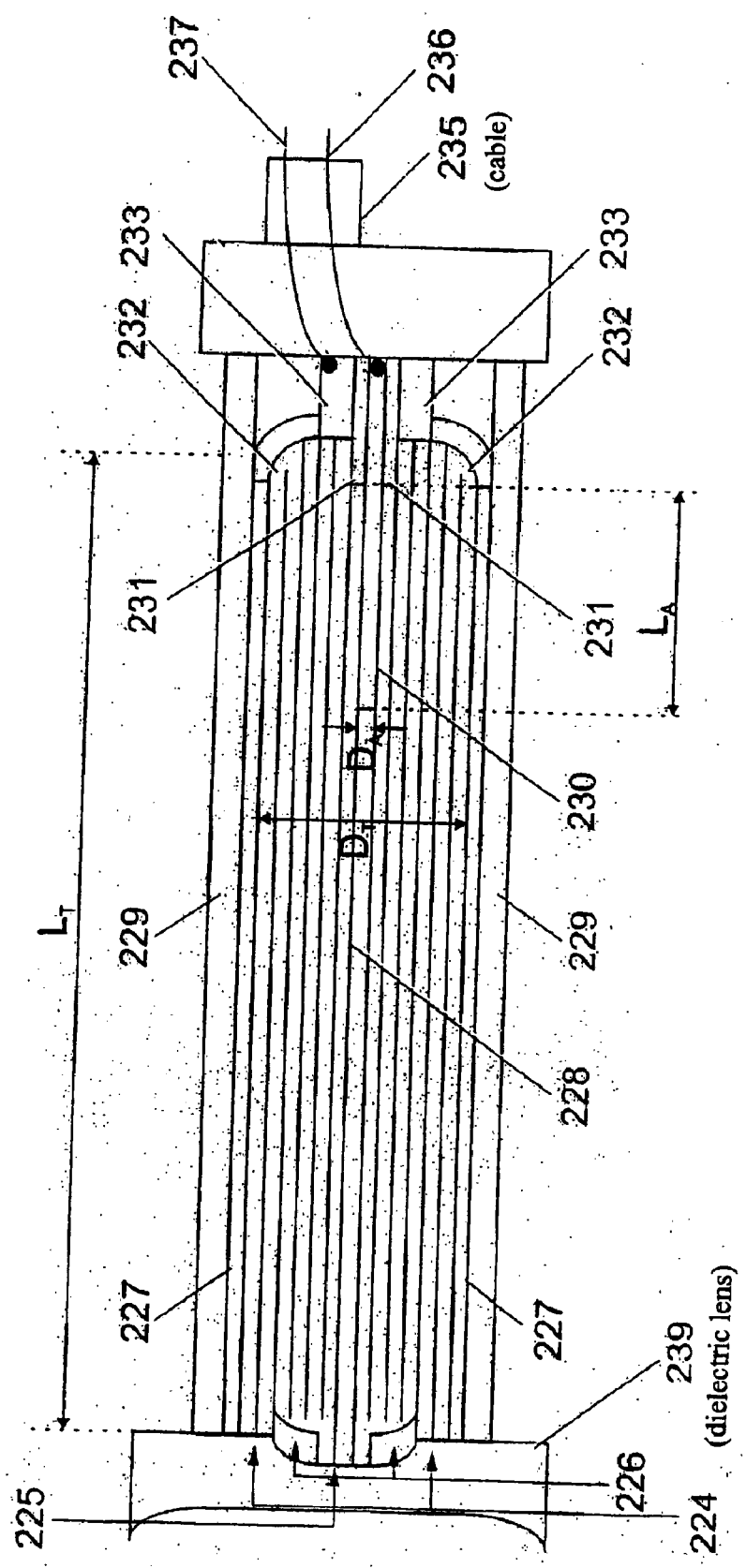
FIG. 5C is a cross-sectional side view of a second variant of the antenna assembly of FIG. 5A.

FIG. 5C shows a further antenna assembly similar to that of FIG. 5A. In this case the assembly is fitted with a cylindrical plano-concave dielectric lens 239. As compared with the embodiment of FIG. 5B, this type of lens attachment further modifies the beam depending on the geometry of the concave surface, in addition to its refractive and dielectric properties. A beam emerging from the embodiment of FIG. 5A will diverge beyond the focal distance of the assembly. A plano-concave lens of this type may be configured to reduce such divergence or to re-focus the beam or to collimate the beam.

Figure 5D:
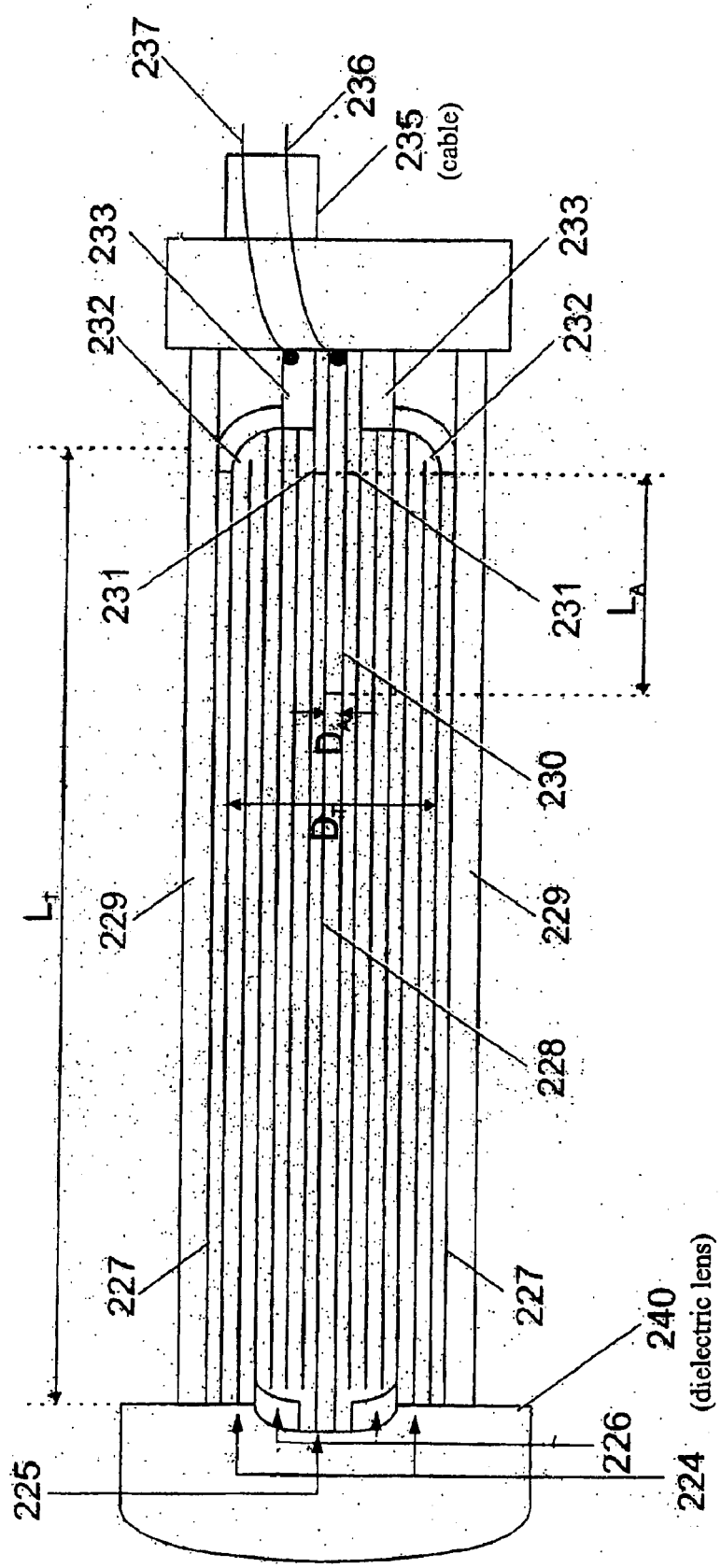
FIG. 5D is a cross-sectional side view of a third variant of the antenna assembly of FIG. 5A.

FIG. 5D shows still another antenna assembly similar to that of FIG. 5A. In this case the assembly is fitted with a cylindrical plano-convex dielectric lens 240. This type of lens attachment will have an effect opposite to that of FIG. 5B. When the assembly is used as a receiver, it will increase the capacity of the assembly to collect incident radiation.

Figure 5E:
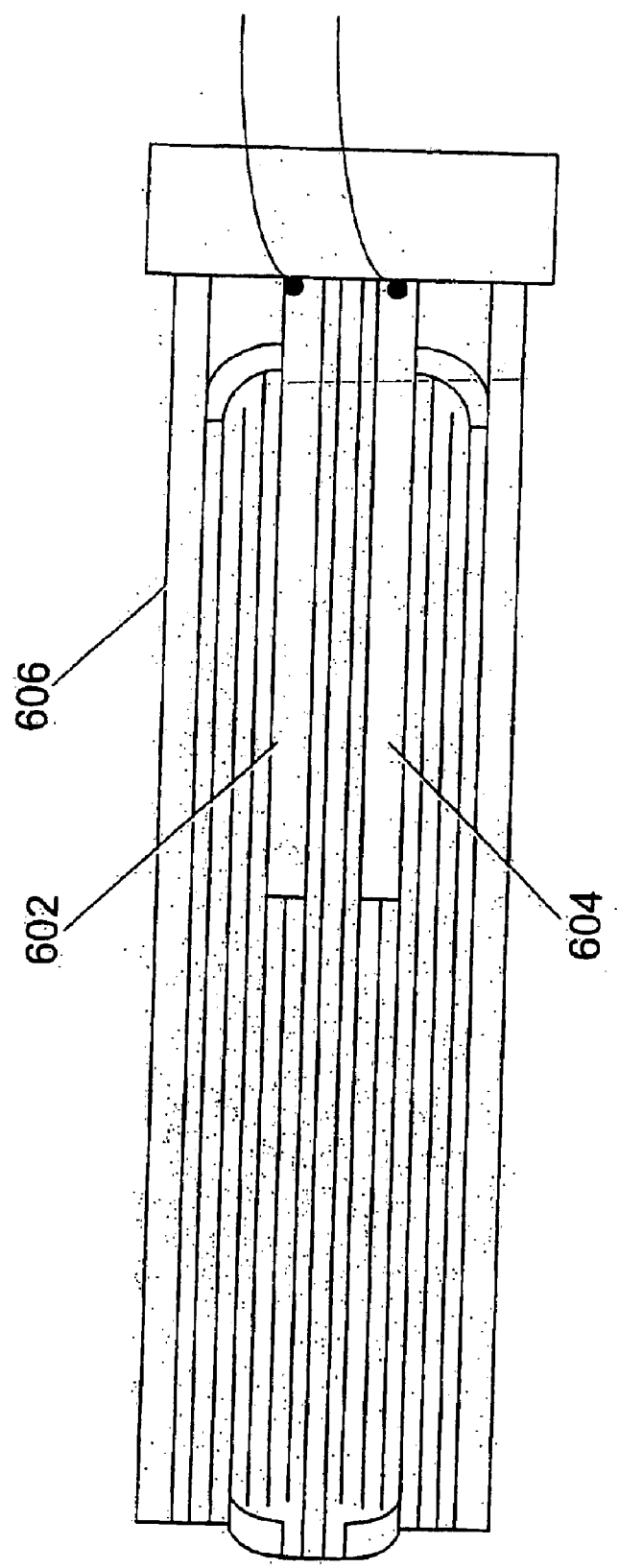
FIG. 5E is a cross-sectional side view of an antenna assembly for use as a transmitter or receiver, similar to that of FIG. 5A.

In the embodiments of FIGS. 5A to 5D, the tubular body of the assembly acts as the cathode of the antenna and the anode extends along the central longitudinal axis of the tube. FIG. 5E shows an alternative embodiment, similar to that of FIG. 5A except that both the anode and cathode both comprise elongate, preferably tubular, elements 602, 604 located inside the outer tube 606, parallel to and arranged symmetrically about the longitudinal axis thereof. The dimensions (particularly the lengths and diameters) of the anode and cathode elements 602 and 604 are preferably proportional to the corresponding dimensions of the tube 606, as with the anode of the embodiments of FIGS. 5A–5D. Also, the spacings between the elements 602 and 604 and between the elements and the outer tube 606 are similarly in proportion.

The arrangement of the antenna elements 602 and 604 in FIG. 5E allows a pair of similar antenna assemblies to be cross polarised relative to one another since the assemblies can be rotated about their longitudinal axes such that the planes in which the elements 602 and 604 of each assembly lie can be arranged at right angles to one another.

Figures 5F, 5G, 5H:
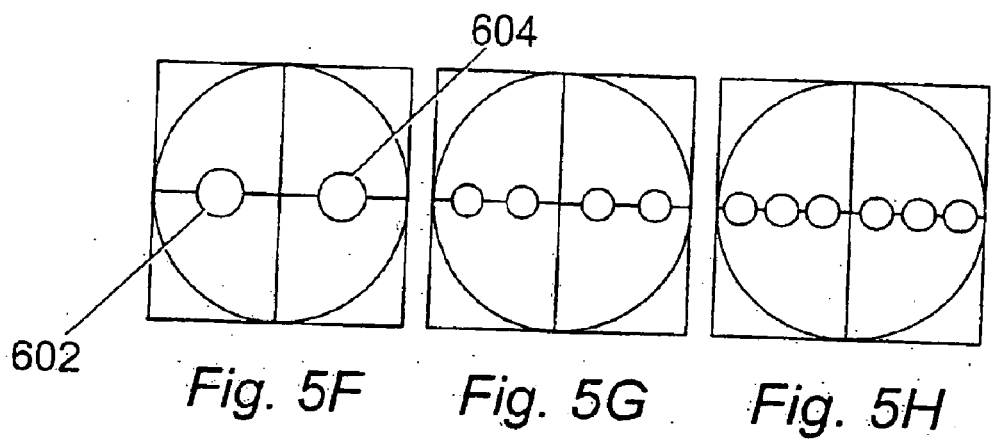
FIGS. 5F to 5N are schematic end views illustrating variants of antenna assemblies of the type shown in FIG. 5E.
Figures 5I, 5J, 5K:
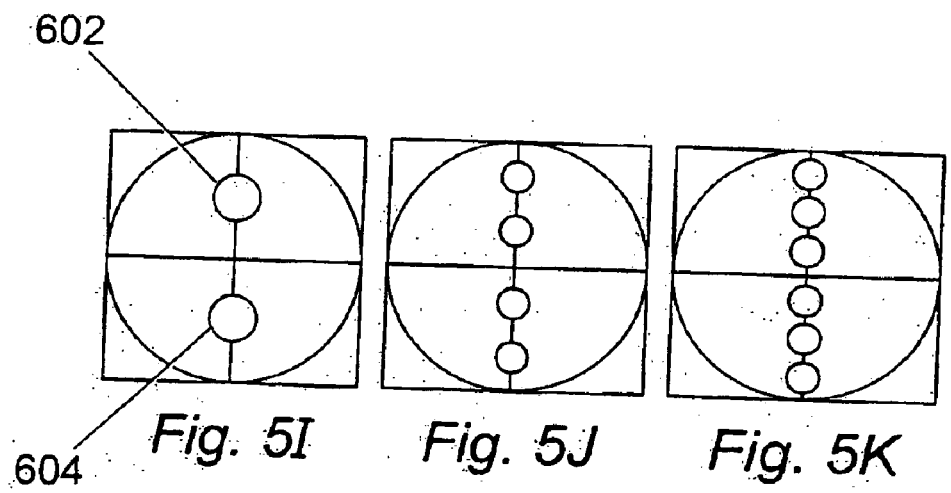
Figures 5L, 5M, 5N:
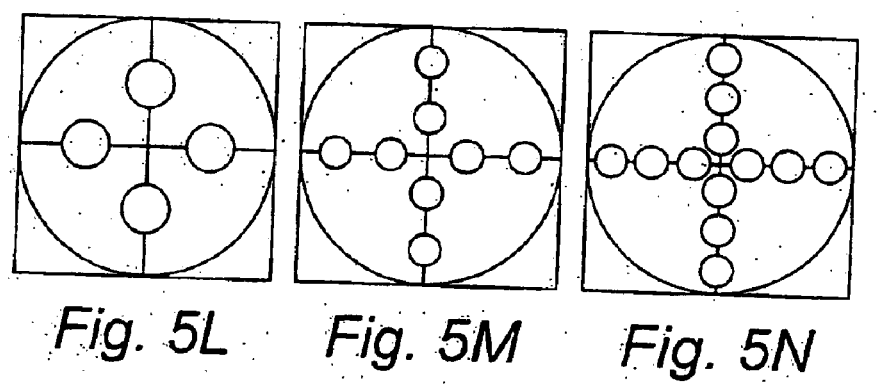

The number and arrangement of anode and cathode elements within the antenna assemblies may be varied, as illustrated in FIGS. 5F to 5N, which are schematic end views of antenna assemblies similar to those of FIG. 5E with different arrangements of elements. FIGS. 5F and 5I show assemblies similar to those of FIG. 5E with one anode and one cathode element 602 and 604. In FIG. 5F, the elements are oriented at right angles to those of FIG. 5I. FIGS. 5G, 5H 5J and 5K show assemblies with multiple anode and cathode elements arranged in linear arrays along a diameter of the outer tube of the assembly, with FIGS. 5G and 5H showing the arrays oriented at right angles to those of FIGS. 5J and 5K. FIGS. 5L to 5N show further embodiments with multiple elements arranged in cruciform arrays, the elements being located along two diameters of the tube at right angles to one another. In such embodiments, the arrangement of anodes and cathodes may vary. For example, the elements along one diameter may all be anodes and the elements along the other diameter may all be anodes, or the elements located along two adjacent radii may be anodes and the elements located along the other two radii my be cathodes, allowing different polarisations of respective assemblies Pairs of assemblies may be oriented with the planes of their arrays disposed at relative angles other than 90°, such as 45°, so as to provide other relative polarisations. Electrical connections to the various elements may be switchable so that a single assembly may be selectively configured with different arrangements of anodes and cathodes. In all cases, the relative dimensions and spacings of the elements and the outer tube are preferably in proportion as previously described.

The various basic modes of operation of radar systems in accordance with the invention will now be described.

Figure 6A:
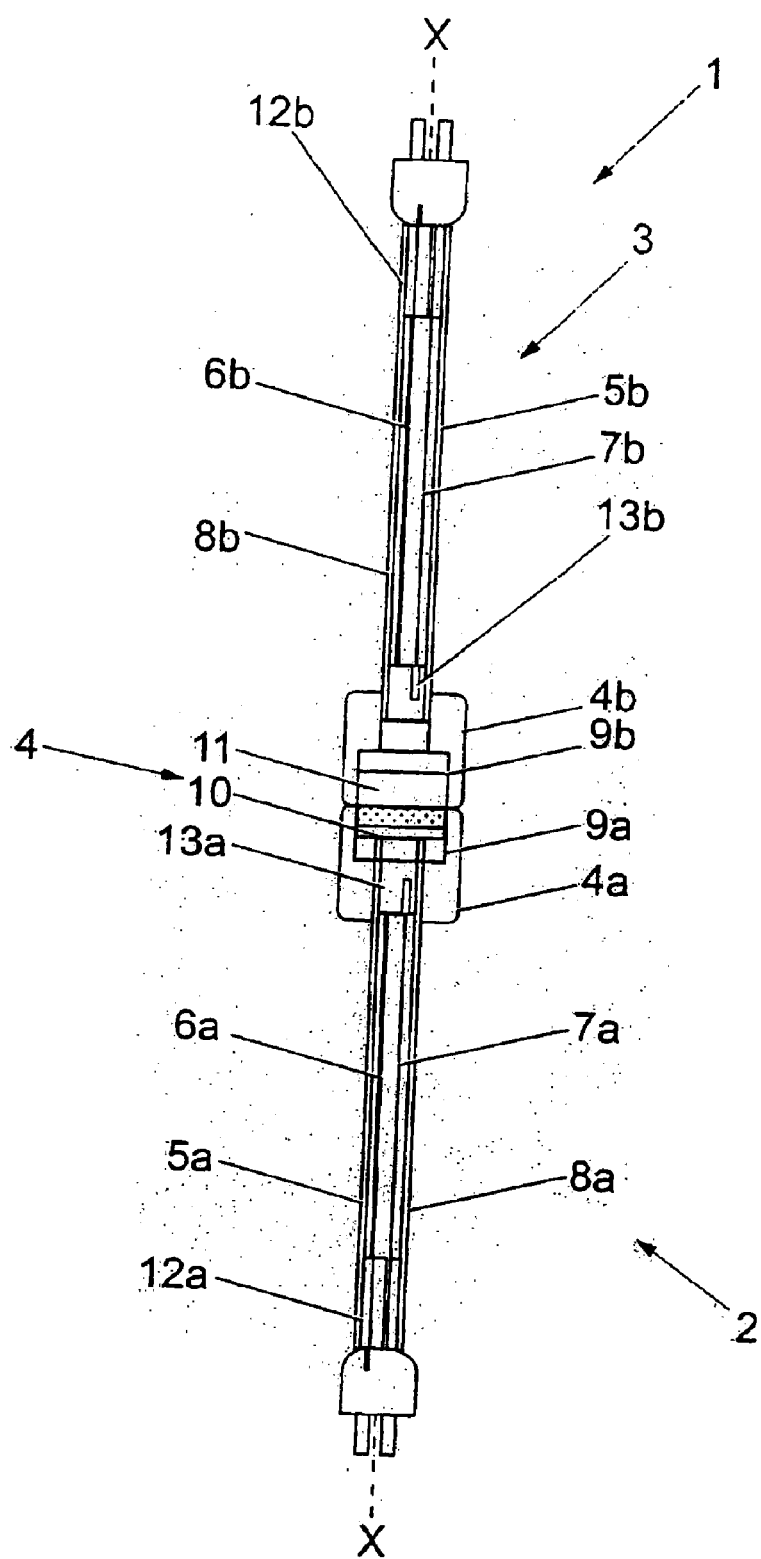
FIG. 6A is a cross-sectional view of radar apparatus set up for chamber mode operation according to one embodiment of the invention.
Figure 6B:
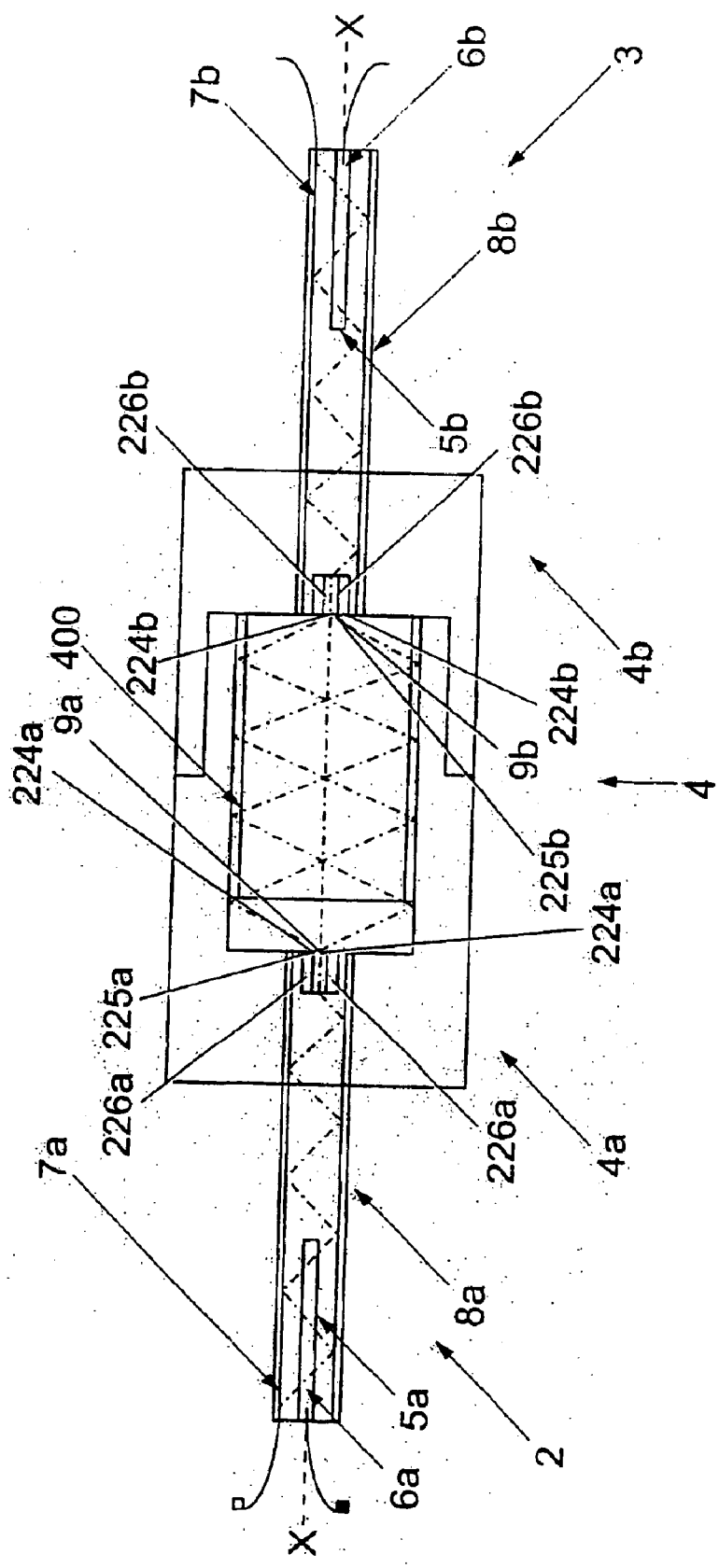
FIG. 6B is a cross sectional view of apparatus set up according to a variation of the embodiment of FIG. 6A.

FIGS. 6A and 6B illustrate "chamber" modes, in which a sample of material or the like is enclosed in a chamber. These embodiments operate by "transilluminating" the sample. The embodiments of FIGS. 3 and 4 are also intended for chamber mode operation, but do not transilluminate the sample in the same way as the embodiments of FIGS. 6A and 6B.

Referring now to FIG. 6A, a cross-section of two antenna assemblies similar to those of FIG. 5E is illustrated, arranged for chamber mode operation.

The apparatus shown generally at 1 consists of a transmitter assembly 2 and a receiver assembly 3 aligned substantially coaxially with a chamber 4 provided in co-alignment therebetween.

The transmitter 2 and receiver 3 each consist of a cavity 5a and 5b respectively, for example a hollow tube or pipe. Within the tube 5a, an anode 6a and cathode 7a form a transmitting antenna 8a which is disposed in longitudinal alignment with the tube axis XX'. Within tube 5b, an anode 6b and cathode 7b form a receiving antenna 5b which is disposed in longitudinal alignment with the tube axis XX'.

Within each tube 5a,5b, the anodes 6a,6b and cathodes 7a,7b are substantially surrounded by a cladding material selected for its dielectric properties. For example, the antennae 8a,8b can be immersed in distilled water which is used as a dielectric cladding. Other alternatives include mixtures of distilled water and sand, or any other substance having the desired dielectric properties. Each tube 5a, 5b is suitably sealed at each end 12a, 13a and 12b, 13b respectively.

A suitable sealant is, for example, a resin or other electrically insulating substance, Focusing means 3a, 9b are provided adjacent to the chamber 4. In this case, each of the focusing means 9a or 9b comprises a dielectric lens of a selected geometry and dielectric composition to enable the radiation emitted/ received by the respective transmitting antenna 8a or collecting antenna 8b to be converged/diverged as it enters/exits the chamber 4 respectively. For example, in this first embodiment of the invention, the lenses 9a, 9b of the transmitter and receiver respectively are both selected to have a wax composition with a high resistivity, for example, of the order of $10^9$ Megohm-meters.

The relative dimensions of each anode 6a,6b to the corresponding cathode 7a, 7b and the surrounding dielectric material and/or tube 5a,5b are determined to be fractionally proportional to each other as previously described. For example, the width of the anode 6a is proportional to the width of the cathode 7a and to the interior diameter of the tube 5a and the length of the anode 6a is proportional to the overall length of the tube 5a.

It is believed that such geometrical scaling between the antenna and the surrounding cladding, together with the dielectric properties of the cladding, assists the formation of resonant standing wave oscillations. Standing wave oscillations set up within the dielectric material contained within the transmitting tube 5 can assist in the intensification and collimation of the emitted radiation. Under such conditions, the transmitter 2 provides a means of generating a resonant and collimated beam of radiation at selected wavelengths which the receiver 3 is capable of detecting.

The overall geometry of the transmitter 2 and receiver 3 are therefore related to the size and scale of resolution required. The dielectric properties of the cladding material selected to surround the antennas 8a, 8b are also important in this respect as these will affect the group velocity $V_g$ of the radiation emitted/received.

In the embodiment illustrated in FIG. 6A, the transmitter 2 and receiver 3 are arranged in coaxial alignment so that the sample chamber 4 is transilluminated.

To typecast a substance by determining its spectral characteristics, other selection criteria may be used to determine suitable antenna cladding materials and the relative dimensions and overall size of the antenna assemblies. In each case the object is to ensure sufficient spectral detail is obtained at the desired resolution and scale. To ensure optimum conditions, it is preferable for the widths/lengths of the tubes 5a,5b to be integral multiples of the widths/lengths of the internal antennas 8a and 8b respectively.

Returning to FIG. 6A, in this embodiment of the invention the radar equipment 1 is operated to typecast/identify a sample 10 placed within the chamber 4. The chamber 4 in this embodiment is disposed in two parts: a lower portion 4a attached to the transmitter 2 and an upper portion 4b attached to the receiver 3. The sample 10 is placed in the lower portion 4a. For example, the chamber may have an internal diameter of 40 mm and an internal depth of 40 mm above the tube base.

In this embodiment, the tubes 5a,5b may each have an internal diameter of 16 mm, and the chamber 4 is positioned so that the overall inner transmission length of the transmitter tube 5a and chamber portion 4a is 330 mm and the overall receiver length of the receiving tube 5b and chamber portion 4b is 295 mm. The measurements in each case are parallel to the direction XX' and are measured from the contact interface between the lower chamber portion 4a and the upper chamber portion 4b when the chambers contact each other in the transillumination configuration. For a required internal chamber volume, the dielectric lenses 9a, 9b are selected to optimise the convergence/divergence of radiation emitted by the antenna assemblies 2,3 and the sample chamber portion 4a is located within a maximum distance from the transmitter 2, preferably no more than 300 mm.

In the embodiment illustrated in FIG. 6A, each antenna 8a, 8b may be a multi-folded YAGI array with two insulated groups containing a plurality of individually screened high quality copper elements in the longitudinal tube plane XX'. Each array is filled with the selected dielectric material, such as distilled water in this example, to make a dielectrically clad bistatic antenna pair. The above configuration enables an optimum impedance match to be obtained at 50 ohm.

The radiation emitted by the transmitting antenna 8a is focused by means of the wax lens 9a so that the sample 10 placed in the lower portion of the chamber 4a is irradiated. Each wax lens 9a, 9b in this embodiment extends 4 mm into the base of the chamber portions 4a, 4b respectively. The receiving portion of the chamber 4b is filled with a suitable dielectric, for example, air. The radiation is refocussed by the wax lens 9b into the receiving antenna assembly 2 where it is detected by the receiving antenna 8b.

In this embodiment, the size of the chamber 4 limits the size of objects to be examined: apart from this limitation a variety of substances may be typecast ranging, for example, from solid materials or composites, liquids, gases, soils, sediments or powder samples. For example, wood powders, soils, flours and oils. Both organic and non-organic substances can be typecast.

As an example, if the total volume of the sample chamber 4 is 45 ml, a sample of, for example, 25 ml of the substance to be typecast may be placed within the lower portion of the chamber 4a. Air occupies the remaining 20 ml volume of space inside the upper chamber portion 4b.

To ensure that stray e.m. radiation is reduced to a minimum, suitable e.m. shielding is provided. For example, by selecting a conductive, metallic substance (e.g. aluminium) to form the tubes 5a,5b and chamber portions 4a,4b and/or by further sheathing the metallic substance with a suitable insulating material (e.g. plastic). The provision of a layer of insulating material and conductive material is as is known in the art such that stray e.m. fields etc. are substantially eliminated.

The transmitter antenna assembly 2 is used to generate a resonant collimated beam of pulsed radar signals. These pulsed signals are set up and controlled by a pulse generator unit as previously described in relation to FIGS. 1 and 2. In this example, the bandwidth of the transmitted pulse may be of the order of 2 MHz to 200 MHz. A large enough time window is employed to ensure that sufficient reflections have occurred within the telescopes 2, 3 and the chamber 4. For example, a time window of 16 ns can be used with a pulse interval time of 100 ms.

FIG. 6B shows another embodiment which is a variation of the arrangement of FIG. 6A. In FIGS. 6A and 6B, like reference numerals designate like or equivalent components and features. In this embodiment, the transmitting and receiving antenna assemblies 2 and 3 are again aligned in transillumination mode, with an enclosed chamber 4 which completely contains and conceals a sample container 400 for specimen typecasting. In this example the transmitting and receiving antenna assemblies may be similar to those of FIGS. 5A and 5B. This embodiment differs from that of FIG. 6A in that interior cavities of the tubes 5a and 5b are packed with a high dielectric material, such as barium titanate, for which $\epsilon_r$ equals 4000 at room temperature. Within the tubes 5a, 5b, the anodes 6a, 6b are located centrally, extending along the axis XX', and the cathodes 7a, 7b are provided by the inner walls of the tubes 5a, 5b.

The focussing means 9a, 9b preferably touch the top and bottom respectively of the sample container 400. In this case, the focussing means 9a, 9b comprises two concentric slit-ring apertures 224a, 224b, 225a and 225b, separated by a spacer 226a, 226b, as described above in relation to FIG. 5.

The chamber 4 in this case comprises two metallic solid cells 4a, 4b screwed together to form a sealed radio frequency (RF) shielded unit. The cells 4a, 4b are preferably made from non-magnetic metals, such as aluminium or brass, for example.

This arrangement of the typecasting chamber has been optimised to substantially eliminate stray electromagnetic fields.

The bandwidth of the signals received depends on the size and configuration of the antennas 8a,8b and the sample chamber 4. If the sample substance is to be typecast, its spectral characteristics are determined by subtracting the signal received from the apparatus under resonant conditions when the sample chamber 4 is empty from the signal received under similar conditions when a substance to be typecast is placed within the chamber 4. The spectral characteristics of the resultant data may then be compared with the spectral characteristics of known materials which have previously been obtained in a similar manner and stored in a database.

It is important to provide a sufficiently long time window for the radiation pattern created within the test chamber 4 to create resonant conditions within the sample (this also applies to other typecasting modes of operation as shall be described below). The transmitted radar pulse may be tuned so that the detected signal indicates that a suitable resonant radiation conditions have been established. The second mode of operation relates to the use of antenna assemblies 200, such as those illustrated in FIG. 5, being deployed in a transillumination configuration, without the use of a sample chamber, such as that illustrated in FIG. 6B, which shows axially aligned Tx and Rx antenna assemblies 201, 202, such as those of FIGS. 5A–5N. It will be understood that transillumination modes of operation do not necessarily require the Tx and Rx antennas to be axially aligned. The antennas may be parallel or at an angle to one another on one side of the object etc under examination, with a reflector placed behind the object so that the signal from the Tx antenna passes through the object and is reflected back to the receiver by the reflector.

Figure 7A:
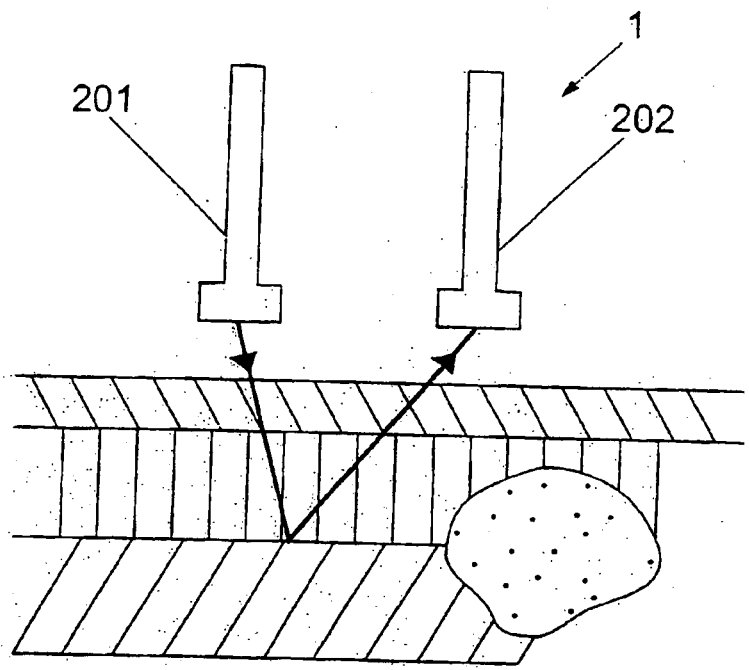
FIG. 7A illustrates an example of an arrangement of radar apparatus for operation in a reflection mode in accordance with a further embodiment of the invention.
Figure 7B:
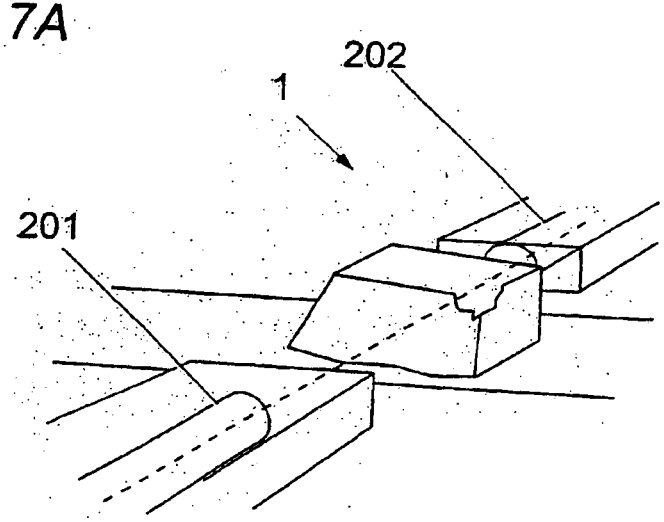
FIG. 7B illustrates a further arrangement of radar apparatus for operation in a transillumination mode in accordance with a further embodiment of the invention.

As shown in FIG. 7B, the assemblies are co-axially aligned to face one another and are placed at an optimal focusing separation with a test substance/object located mid-way between the two sensors in order to achieve a balanced transillumination effect. Assemblies of this type may also be used in the arrangements illustrated in FIGS. 6A and 6B.

In this mode, the apparatus provides a means to image or typecast the internal composition or contents of, for example, baggage on a conveyor belt. In such an application, the antenna assemblies 201, 202 are arranged on either side of the belt to transilluminate baggage as it moves along the belt. Metallic reflectors may be further provided below the belt and around the sides/roof of any surrounding shield.

The third mode of operation relates to the antenna assemblies 200 being deployed in a parallel configuration or at an angle to one another with the apertures of the Tx and Rx antenna assemblies facing the same direction and the received signal having been deviated back towards its source direction (e.g. reflected or backscattered). FIGS. 7A, 8A to 8D, 9 and 10 illustrate examples of this mode of operation. The antenna assemblies may be deployed in a stationary configuration or one or both of the antenna assemblies may move relative to the substance/area to be scanned and/or the substance/area may be moved relative to the antenna assemblies.

For example, FIG. 7A is a schematic diagram illustrating the arrangement of the receiving and transmitting antenna assemblies 201, 202 as described above, in a GPR application suitable for remotely detecting and/or imaging and/or typecasting objects and/or substances located underground. The transmitter assembly 201 and the receiver assembly 202 may be mounted on suitable land and/or sea vehicles. For example, FIG. 8A illustrates how the apparatus may be mounted on to the rear or front of a land vehicle. Alternatively, the apparatus could be provided to protrude through the floor or hull of a sea-vehicle such as FIG. 8D shows. Depending on the scale of the antenna assemblies, the apparatus may be highly portable for applications, such as FIGS. 8B and 8C illustrate. FIG. 8B shows a portable device suitable for operation on land whereas FIG. 8C shows a portable device suitable for submerged operation by a diver.

Figure 9:
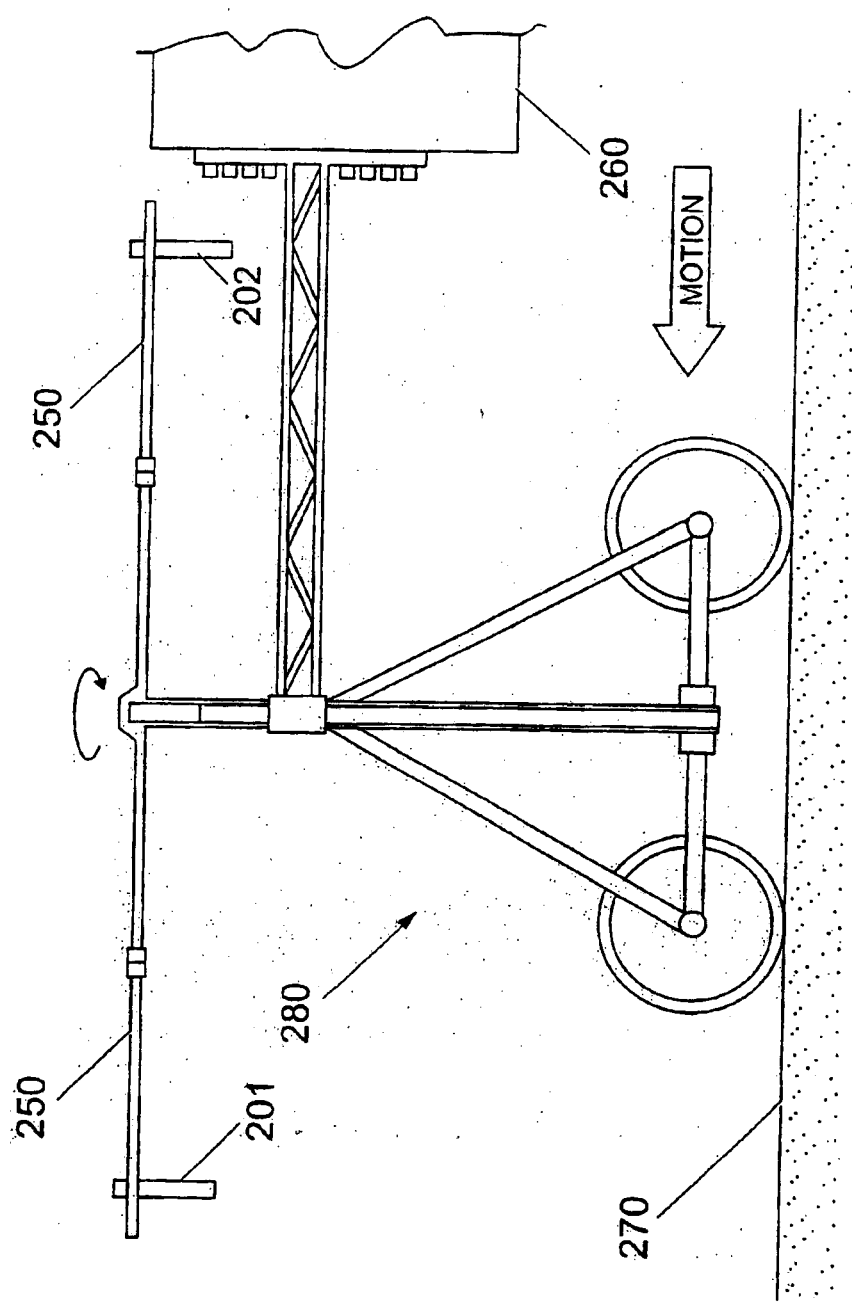
FIG. 9 is a sketch illustrating an embodiment of radar apparatus in accordance with the invention suitable for sea-bed scanning.

FIG. 9 illustrates how a transmitting antenna assembly 201 and a receiving antenna assembly 202 may be arranged in parallel along a tong 250 forming part of a submerged moveable platform 280 which can be attached, for example, to the front of a remotely operated vehicle 260 suitable for operation on a seabed 270.

Figure 10:
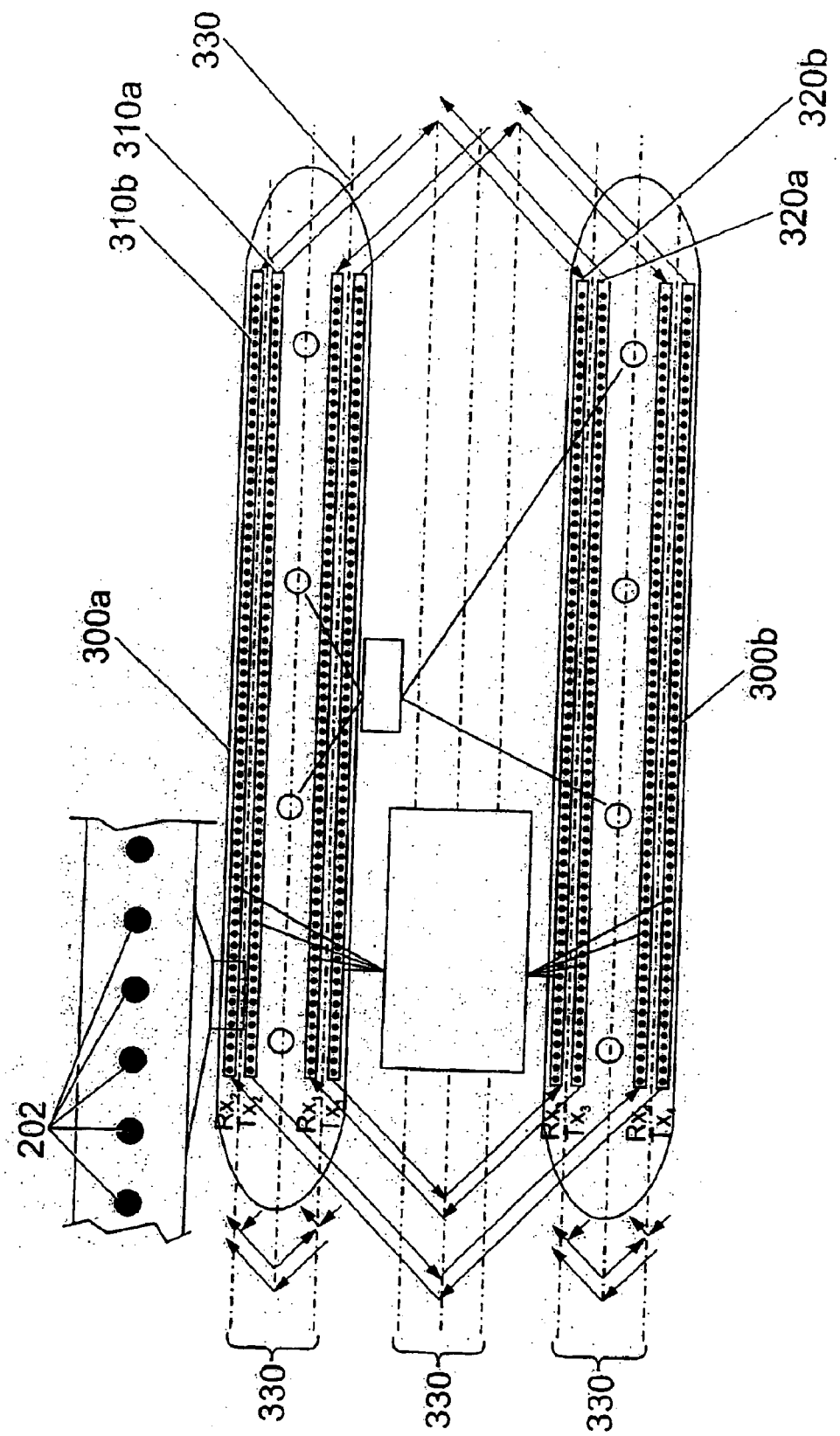
FIG. 10 is a sketch illustrating another embodiment of apparatus embodying the invention suitable for sea-bed scanning.

FIG. 10 illustrates how a plurality of pairs of arrays of transmitting antenna assemblies 201 and receiving antenna assemblies 202 may be arranged on the underside of pontoon-type supports 300a, 300b for use with a semi-submersible platform or sea-vehicle. Such a configuration of the radar apparatus enables sea-bed sensing, imaging and typecasting of materials for the oil industry.

The antenna pairs are spaced along the pontoon, preferably equidistant from adjacent antenna pairs in the array. At least one array of receiving antennas is arranged parallel to the corresponding array of paired transmitting antennas to enable wide angle reflection and refraction (WARR) sounding At least one such antenna pair array 310a,310b and 320a,320b is provided on each pontoon, for example, two per pontoon are illustrated in FIG. 10, to form a total of eight arrays of antenna assemblies. Using this apparatus, a variety of large scale structural and compositional information may be collated from and within the seabed, for example, the apparatus may be used in such a "searching mode" to detect subterranean and seabed features.

The inventor has detected shipwrecks and the apparatus may be suitable for the detection of oil and gas deposits using this apparatus. Features such as shipwrecks may be buried deep below the seabed. Although it is possible to detect such features with a single pair of antenna assemblies over a relatively small search area, an array of antennas, and preferably a multiple array of antennas can be used. Multiple arrays could scan many lines in one forward sweep covering a large search area in a short space of time.

Furthermore, by allowing the apparatus to remain in situ and scan a fixed area for a period of time, (i.e. to "stare" in the surveying mode) it is possible to record a series of images indicating movement of substances such as liquids (e.g. oil) and gases (e.g., natural gas seepage).

In the WARR configuration illustrated in FIG. 10, the arrays provided operate in tandem. For example, the transmitting array 310a will emit signals which are reflected and recorded by the receiving array 320b, and the transmitting array 320a will emit signals which are preferably recorded by the receiving array 310b, etc. This enables a plurality of lines 330 to be scanned efficiently along the sea-bed. In the illustrated example, nine lines 330 can be scanned. In WARR mode any antenna assembly can be selected as a transmitter and reflections can be received from any receiving antenna in any specific order and sampling time to allow increasing Tx and Rx (see FIG. 10) separation for triangulation and precision mapping purposes. If this triangulation procedure is carried out, then a detailed table of dielectric properties can be produced including depths, radar velocities, interlayer thicknesses, interlayer velocities, and interlayer dielectric constants.

The sizes of the apertures of the antenna assemblies may be optimised to suit the oath length and the beam collimation requirements. For deeper sounding and longer path lengths it may be necessary to vary the focusing means, for example by fitting narrow apertures with a range of optional circular slits. These can then be fitted to the telescopes to provide focusing at the optimum near/far field ranges. Dielectric lens attachments such as those illustrated in FIGS. 5B to 5D may also be used for these purposes. The focusing means selection criteria follows that known in the art from radar design and selection procedures and are based on simple geometric, timing and platform speed considerations.

For field operation, typical land vehicles include ATVs, small robotic platforms, man-portable and/or hand operated or track or rail mounted for tunnels or mines, or man portable operated from raised bucket platforms for scanning vertical wall surfaces of buildings, tunnels or bridge structures. Typical sea-vehicles include inflatables, hovercraft, Dory work boats, tugboats, hydrographic/seismic-type survey vessels, or oil-industry semi-submersible platforms with pontoons suitable for mounting large tube-arrays, or ROVs, or autonomous underwater vehicles (AUVs), or Jack-Up Platforms or Drilling Rigs or Stand-Alone Production Platforms. The antenna assemblies are typically arranged substantially vertically and are orientated so that they can stare into the ground/seabed, at depths capable of resolving oil and gas reservoir structures. In a specific example for detecting sub-seabed substances, the antenna assemblies 201, 202 may be of the order of 24 m long by 8 inches internal diameter and may comprise two 12 m long by 8 inch (internal diameter) high quality steel oil tube casings welded to another two 12 m by 8 inch casings to make a pair of large transmitting and receiving assemblies some 24 m long. Such a geometry for the antenna assemblies is believed by the inventor to have a natural resonance which amplifies the radar signal by a factor of 180.

The apparatus may be further mounted on air/space vehicles, for example, small helicopters or remotely powered vehicles (RPVs) such as model aircraft, or balloons, blimps or piloted auto-gyros. Spaceborne platforms may be used for subsurface geological investigations of moons, comets and/or other planets.

The selection of appropriate antenna configurations and aperture sizes enables different scales to be resolved, for example, objects/substances which are underground or underwater (see for example, FIGS. 8C, 8D, 9 and 10).

Figure 11A:
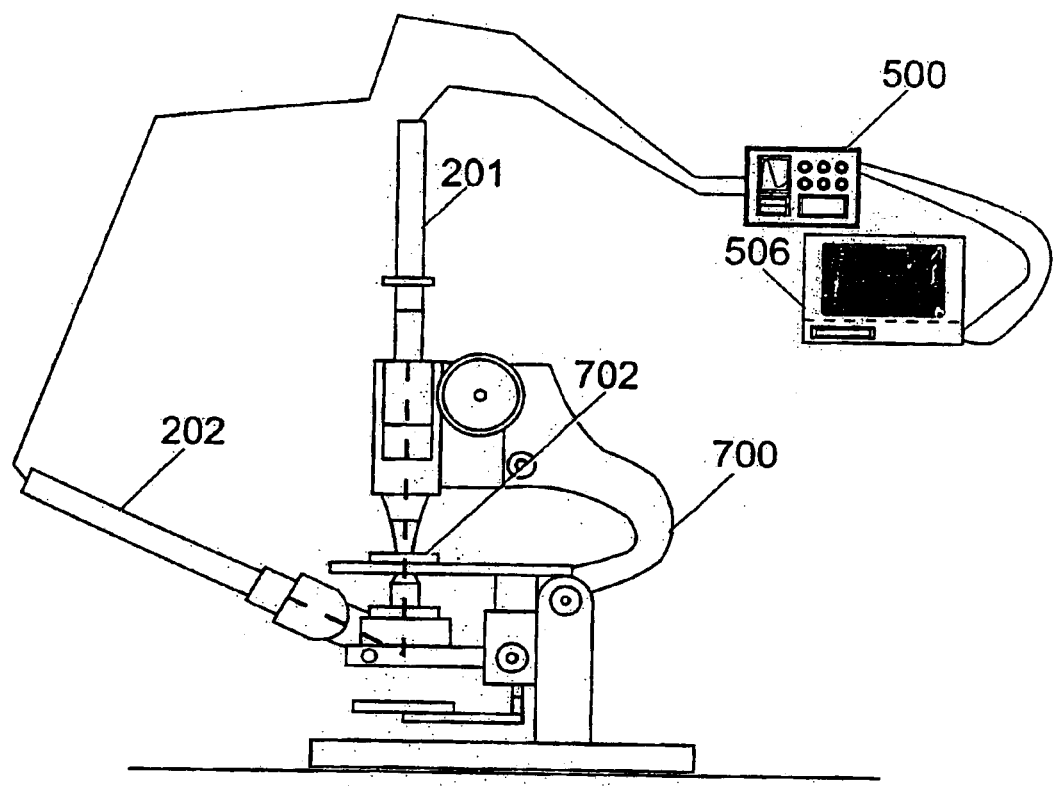
FIG. 11A shows an example of a microscope fitted with transmitting and receiving antenna assemblies in accordance with a further embodiment of the invention.

FIG. 11A illustrates a further embodiment of the invention with a Tx antenna assembly 201 and an Rx antenna assembly mounted on a conventional optical microscope 700, for the purpose of examining, for example, biological samples mounted on microscope slides 702. The Rx assembly 202 is mounted in a socket of the microscope which would normally be occupied by an ocular (eyepiece). The end of the Rx assembly 202 may be suitably configured to fit this existing socket. The Tx assembly 201 in this example is mounted in a socket or the like which would normally receive a light source for illuminating the slide 712. If the microscope is of the binocular type, the other ocular may be used for visual observation of the slide and for focussing the microscope. The transmitted signal from the Tx assembly 201 follows the normal optical path through the microscope to the Rx assembly 202. That is, the Tx and Rx assemblies 201, 202 are arranged for transillumination of the slide 702. Alternatively, the Tx and Rx assemblies could be mounted side by side in the ocular sockets of a binocular microscope, for reflection mode operation. In this way, a variety of different types of optical microscope may be adapted for operation as "radar microscopes" and may be used for imaging and/or typecasting of biological samples or the like in a variety of applications including medical diagnosis. For scanning purposes, the slide 702 may be translated relative to the Tx and Rx assemblies by using the conventional movable slide stage of the microscope.

For precision mapping applications of the invention, it is necessary to employ calibrated antenna assemblies, preferably of the type illustrated in FIGS. 5E to 5N, whose relative separation can be varied for optimised triangulation of range distance. Preferably, the transmitting, Tx, and receiving antennas, Rx, can be rotated about their longitudinal axes through 0–360° relative to one another to enable variable polarisation of signals, so as to optimise coherent image reflections of targets and interfaces of interest.

The triangulation factor is important for many applications of the invention. The polarisation factor is of greatest significance for close range inspection of structures such as pipes or concrete sections. Changing the polarisation, by a factor of 90° for example, can enable the collection of multivariate image-data sets along each scan line. This often assists the classification of the medium and provides co-ordinates of point targets or structures in the medium being investigated.

The antennas can typically be oriented in two ways: plane polarised (PP or Plane Mode) or cross polarised (CP, 90° mode) where Tx is oriented at 90° to Rx or vice versa. Therefore, at any given frequency, two different sets of spectral reflection data (or digital image bands) can be collected. The design of suitable spatial frequency filters and the use of principal components analysis (PCA) for multivariate image mapping of such complex multi-spectral and multi-polarised image datasets can greatly assist in identifying, for example, engineering structures of interest for precision mapping and classification.

Consideration must also be given to the spatial (X,Y,Z) co-ordinates of both the transmitting and receiving antennas. This means that the area to be investigated should be precisely surveyed to build up a concise topographic survey database of co-ordinates for each line scanned. In cases where the scanning lines are non-linear, it is important to track the antennas on their scanning platform during the data collection phase.

This situation may arise, for example, when scanning the irregular topographic features of a biopsy specimen, as the antennas will be mounted on a simple biopsy scanning platform (BSP) and not in direct contact with the surgical specimen. With a fixed antenna configuration on a BSP, where the tissue is irregular, the air gap between the antenna and the specimen will vary considerably. Therefore, it is important to simultaneously track the antennas during the scanning phase so that the true subject datum plane is known and can be related to precise X, Y and Z coordinates of the subject being investigated.

To achieve coherent imaging, it is important that the optimum scan configuration of the antennas is selected. Essentially, this is the fixed separation distance between the Tx and Rx antennas mounted on the scanning rig or BSP. For imaging of deeper structures the antennas have to be fixed with a wider separation distance. Again, for focussing through lower dielectric materials or deeper organs in the body, the antennas should be moved further apart. To acquire accurate depth data it is important to triangulate every scan line, in the body's sub-surface domain. This can be achieved by overlapping scan legs from the start of scan position (SOS) to the end of scan position (EOS). This type of scanning is commonly referred to as a WARR scan (wide angle reflection and refraction, as illustrated in FIG. 11A which shows a fixed Tx antenna assembly 201, and a movable Rx antenna assembly 202 moving progressively away from the Tx antenna 201 in the direction of the arrows, relative to a subject 704, such as a cancer tumour within a body). This can be achieved by automatic sensor array digital switching, managed by software control.

As the scanning rig moves along the scan line, the Rx antenna assembly captures each new reflection and plots the returns alongside the previously scanned returns. This process integrates reflection traces and eventually a comprehensive image of the subject 704 is obtained. To compose a coherent image, the system processes the response reflections from the objects examined. These are automatically enhanced to optimise desired targets and layered boundary reflections may be classified.

The images may also be suitably scaled by software, with re-sampling and auto-zoom features enabling 2-D and 3-D visualisation of point targets and boundary interfaces, displayed in real time These features, together with the use of classified colour palettes, can discriminate the textural classes or surface roughness (for example) of a wide range of materials. A typical breast carcinoma may consist of six distinct tissue layers, with layer thicknesses measured in micrometers (e.g.: 76, 76, 152, 202, 88, 77), each with a different dielectric constant.

Further analysis of the image may display dielectric tables showing mean inter-layer thicknesses, depths, propagation velocities and dielectric constants. These tables may also include RMS error computations in two way travel time measured in nanoseconds (NS) and depth in metres (m) for each stratigraphic boundary.

The preferred signal processing software performs real-time de-convolution of the transmit pulse to allow true conformal mapping of object shapes. For example, conventional GPR reflections from circular or elliptical section structures such as pipes occur as parabolic echoes from the top and bottom of the pipe reflecting surfaces, whereas mapping in the manner described above will display the structures in their true circular or elliptical shapes.

From the resultant images, materials can be spectroscopically identified and classified (as described further below), provided they have been previously typecasted and their spectral characteristics logged in the reference database. If this is the case, classification is possible in near-real-time; that is, within a few micro-seconds of data capture. Depths can be automatically calculated by the system computer after the WARR results have been implemented. Thus, it is simply a matter of reading the depth of a required target position from the scaled image.

FIG. 12 is a table summarising system specifications for a variety of operational modes of systems embodying the invention. Fifteen modes of operation A1–A5, B1–B5 and C1–C5 are indicated, exemplifying the broad range of applications of the invention. Modes A1–A5 are close range/near field (small scale) modes for a range of increasing distances between the Tx antenna and the subject, suitable for applications such as biological and medical imaging.

Modes B1–B5 are near to medium range (medium scale) modes, again for a range of increasing distances, suitable for typical GPR applications with relatively shallow penetration. Modes C1–C5 are long range (large scale) modes, suitable for geological/geophysical applications, particularly in the oil industry, for relatively deep subsea/subsurface penetration. The various modes would typically use substantially the same computer, pulse generator and radar control apparatus, with different Tx and Rx antenna assemblies, these preferably being of the types illustrated in FIGS. 5A to 5N, smaller assemblies (e.g. about 200 mm to 300 mm in length) being used for modes A1 to A5, intermediate size assemblies being used for modes B1 to B5, and larger size assemblies (e.g. up to about 24 m in length) being used for modes C1 to C5.

The resolution time and resolution space (columns 2 and 3) indicate the resolution which may be obtained using each mode. Values given are for salt water and may be converted for other media with different dielectric properties. Column 4 indicates suitable values of the Pulse Repetition Frequency (PRF) for each mode, being higher for close range applications and lower for longer range applications. Column 4 indicates suitable Pulse Width (Pw) values for the various modes, these being shorter for close range modes and longer for long range modes. For each of modes A1–A5, suitable values are in the range 10–100 ps (picoseconds) i.e. 0.01 to 0.1 ns (nanoseconds); for each of modes B1–B5, suitable values are in the range 1–10 ns; for each of modes C1–C5, suitable values are in the range 10 to 25 ns. The table of FIG. 12 utilises Pw values of 0.1 ns for modes A1–A5, 1 ns for modes B1–B5 and 10 ns for modes C1–C5. Column 6 indicates the Time Range (TR) in the received signal produced by each transmitted pulse which will contain data of interest at the relevant distance and scale. The Time Range would normally begin with the first peak of the received signal. The Time Range is shorter for close range/small scale applications and longer for long range/large scale applications.

Columns 6 and 7 indicate the preferred frequency ranges (Fmin to Fmax) of the transmitted pulse for each mode, being higher for close range/small scale applications requiring little penetration and high resolution and lower for long range/large scale applications requiring deep penetration and lower resolution. The frequency range is determined by the radar system as a whole, including the characteristics of the TX and Rx antennas. Columns 9 to 11 indicate suitable values of pulses-per-trace (Ptr), scan rate (SR, traces-per-second) and Sdelay (1/SR)for the purposes of sampling, storing and displaying digitised data.

The total frequency range of the radar systems is indicated as 1 MHz to 10 GHz, which covers an exceptionally wide range of frequencies. This range is suited for the various imaging and typecasting operations of the apparatus at various distances and scales. For each of the fifteen modes, the sampling rate (Fs) most preferably equals two times the maximum frequency (Fmax) as indicated in column 7 of FIG. 12B. The sampling rate is determined by the difference in time delays from pulse to pulse. For all modes of operation, the sampling rate preferably falls in the range Fmax/4 to 4Fmax. The sampling time, Ts (column 12), is different from the sampling rate, being the time during which the analogue signal is sampled before being digitised, corresponding to the time represented by one pixel in the y-direction. Preferably, on average, the sampling time Ts is 1/(2Fmax) It should be at least 1/Fmax but for fast scanning it is recommended to be 1/(4Fmax) which equates to 0.25 ns where Fmax=1 GHz.

It is important that the analogue input signal is filtered before sampling to avoid aliasing. This is partially accomplished by the sampler 516 (FIG. 2) which averages the signal over the sampling time. The lower frequency range is limited by the Tx and Rx antennas, the time window and a low frequency component from the radar. The lowest frequency that can be resolved is the reciprocal of the time from time zero to the end of the trace. For example, consider mode A5 of FIG. 12. In this case, the 25 ns time range (column 6) will have a minimum frequency of $(25\ ns)^{-1}$, i.e. 40 MHz. This is an absolute minimum value. For practical purposes, a higher value (100 MHz in FIG. 12) is preferably selected.

Modes A1 to A5 are intended for close range or near field imaging and typecasting such as in medical and biological applications. The recommended frequency ranges for these modes of operation is from a minimum frequency (Fmin) in the range 100 MHz (A5) to 1 GHz (A1) to a maximum frequency in the range 1 GHz (A5) to 10 GHz (A1). For these frequency ranges, the sampling rate (Fs) is determined by the difference in time delays from pulse to pulse. As noted above, the criterion for selecting Fs is that it should be at least two times Fmax for most applications, or preferably four times Fmax for some specific applications such as fast scanning. The preferred overall range for all modes is Fmax/4 to 4Fmax.

The pulse repetition frequency (PRF) is the rate at which pulses are emitted from the transmitter. For close range (focussed near field imaging) medical and biological applications, PRF should be at least 64 kHz for combined imaging and typecasting applications, but the preferred maximum value is 100 kHz.

The number of pulses per trace (Ptr, column 9, FIG. 12B) is important for efficient operation of the apparatus. The preferred maximum Ptr for modes A1–A5, to cover a wide range of diagnostic medical, biological and biochemical applications, is 100 pulses per trace. The maximum time window, TR, is a function Ptr and Ts, as follows: TR=(Ptr× Ts). Accordingly, in mode A3 operation: Ts=1/2Fmax; i.e. Ts=$10^{-10}$=0.1 ns; TR=(100×0.1)ns=10 ns.

There is a trade off between parameters for optimum imaging and typecasting performance. Higher values of Fmax always give better results in terms of resolution etc. but at the expense of penetration, data processing etc.

Modes B1–B5 relate to near range to medium range (focused subsurface imaging) general ground penetrating radar (GPR) applications. For these modes, the preferred value of PRF is also 100 kHz. The optimum range of Ptr to cover this range of applications is 4000 to 9600 pulses per trace.

Modes C1–C5 relate to medium range to long range (far field) applications. For many far field geological applications, a most appropriate time range would be of the order of 20000 to 80000 ns. For deep geological applications (i.e. shallow seismic to deep seismic type depths up to thousands of metres), the time ranges of the order of 160000 to 250000 ns may be selected.

Stacking the pulse (St) is a common method of enhancing the imaged products in conventional geophysical or seismic imaging. This technique can be applied in the present system at the time of data collection (through digital control) or it can be carried out externally by post-processing of the collected radar imagery. In the latter case, then the data collection rate is preferably increased.

The scanning rate (SR) equals the number of traces (or scans) per second. The maximum value of SR equals PRF divided by the product of Ptr and St. For example (mode A1), where Ptr equals 40, PRF equals 100 kHz and St equals 1 (no stacking), then SR=$(100×10^3)/(40×1)$=2500 scans per second.

With reference to the setting up of the radar system for operational use, the time zero ($T_0$) position is of particular importance. $T_0$ will generally be selected as appropriate for a particular application, to ensure that all of the relevant received signal data is retrieved. In general terms $T_0$ is the time at which the transmitted pulse is received by the shortest transmission path between the transmitter and the receiver (the "direct wave", e.g. transmitted through air in an air medium or through water in a water medium) The required To position is not actually the zero point on the time scale because the pulse has travelled from the transmitter unit to the receiver unit, so the $T_0$ position actually corresponds to the distance between the transmitter antenna and the receiver antenna divided by the speed of the pulse. This factor is important for obtaining accurate depth measurements through materials, especially those with multivariate dielectric constants and inter-layer velocities. It is important that the $T_0$ position is included in the time window range (TR, column 6, FIG. 12) or in the displayed image on the visual display unit of the computer. The direct wave received pulse can be used to de-convolve the image. This will generally produce a less cluttered image; i.e. objects such as circular section pipes will appear circular rather than as parabolic reflections of the top and bottom of the pipe.

The position of $T_0$ in the image depends on the various delays in the radar system and is preferably set up when the radar is first switched on, before any other settings are altered.

The foregoing discussion, referring to FIG. 12 of the drawings, applies particularly to transillumination and reflection modes of operation.

To set up appropriate conditions in order to typecast material in chamber mode operation (as illustrated in FIG. 6A), the following technique may be used when using a conventional GPR radar set (or equivalent) as the pulse generator. To provide optimum control during the set up procedure, the best method found by the inventor is to switch off the Automatic Gain Control and the Time Varying Gain Control of the pulse generator 21 (FIG. 1) A reasonable received signal bandwidth is then established by suitable selection of the cutoff frequencies of a high-pass filter and low-pass filter; for example, between 40 Hz and 3.2 kHz.

A large enough time window is selected for sampling to allow a sufficient number of resonant ringing reflections through the scanned substance/object to have occurred to enable significant spectral relationships for each sampled substance to be established. The inventor has found that in the case where a 25 ml sample was placed in the chamber portion 4a (FIG. 6A), and 20 ml of air was left in the sample chamber portion 4b, that a suitable time window was approximately 16 ns. Increasing the minimum time window to, for example, 25 ns, further enables sufficient resonant effects to be established and tested. The sampling interval, or scan rate, is selected to allow a sufficient pulse dwell time to enable resonance through the sampled substance to be optimised. In this example, sampling was optimised with a sampling interval of 100 ms (10 scans per second) to ensure that consistent results were obtained on repetitive tests. In general, as a lower limit, the sampling interval should not be less than 50 ms; i.e. the scan rate should not exceed 20 scans per second. However, for certain fast scanning applications, it is possible to scan at 200 scans per second and it is also possible for typecasting to be performed at this rate.

The data obtained using the apparatus, systems and methods as described thus far may be used for a variety of purposes, including imaging, mapping, dimensional measurement, and typecasting (identification of materials etc.).

The time domain data as received by the receiver may be processed for imaging/mapping/measurement purposes using well known techniques employed in conventional GPR and other imaging/mapping applications, which will not be described herein.

The time domain data may be transformed into frequency domain data, by means of Fourier Transform techniques (especially FFT). This provides an energy/frequency spectrum which, in accordance with one aspect of the invention, may be used as a unique signature to identify (typecast) the material which produced the spectrum. In accordance with this aspect of the invention, the energy/frequency spectrum is analysed using any of a variety of well known statistical analysis methods (such as principal components analysis, maximum likelihood classification or multivariate classification) or combinations of such methods, in order to obtain a parameter set. A reference database of known materials is established, comprising the original time domain data, and/or the transformed data, and/or the parameter set obtained therefrom, and an unknown material can thereafter be identified by comparing its parameter set, also obtained by means of the apparatus, systems and methods of the present invention, with those in the reference database. The statistical analysis of the energy/frequency spectrum may be performed either by frequency classification (using energy bins) or by energy classification (using frequency bins).

Conventional analytical methods may also be applied to the data for classification purposes, such as time domain reflectometry techniques, velocity distribution analysis or the like, as used in conventional geophysical applications for determining dielectric properties.

The computer forming part of the radar system in accordance with the invention may be programmed to perform these functions.

By use of the invention, it is possible to classify and map oil, water and gas reserves deep underground without the need for drilling. By staring deep underground, it is possible to monitor oil, water and gas movements and to classify oils already typecast and held in reference databases of oil types etc.

Other applications include the detection of explosives, contraband substances, and in particular narcotics, as well as the typecasting of rock, soil, sediment and ice cores, and biological/medical imaging and diagnosis.

The preferred antenna assemblies of the present invention (FIGS. 5A to 5N) are believed to operate in a manner analogous to a laser, except that radio waves are resonated in a highly dielectric medium and with a carefully selected dielectric medium and with a carefully selected dielectric lens aperture with concentric circular focusing slits. With a 3 mm aperture, it is possible to focus the beam from 3 mm outside the central aperture to infinity, like a pin-hole camera.

Figure 11B:
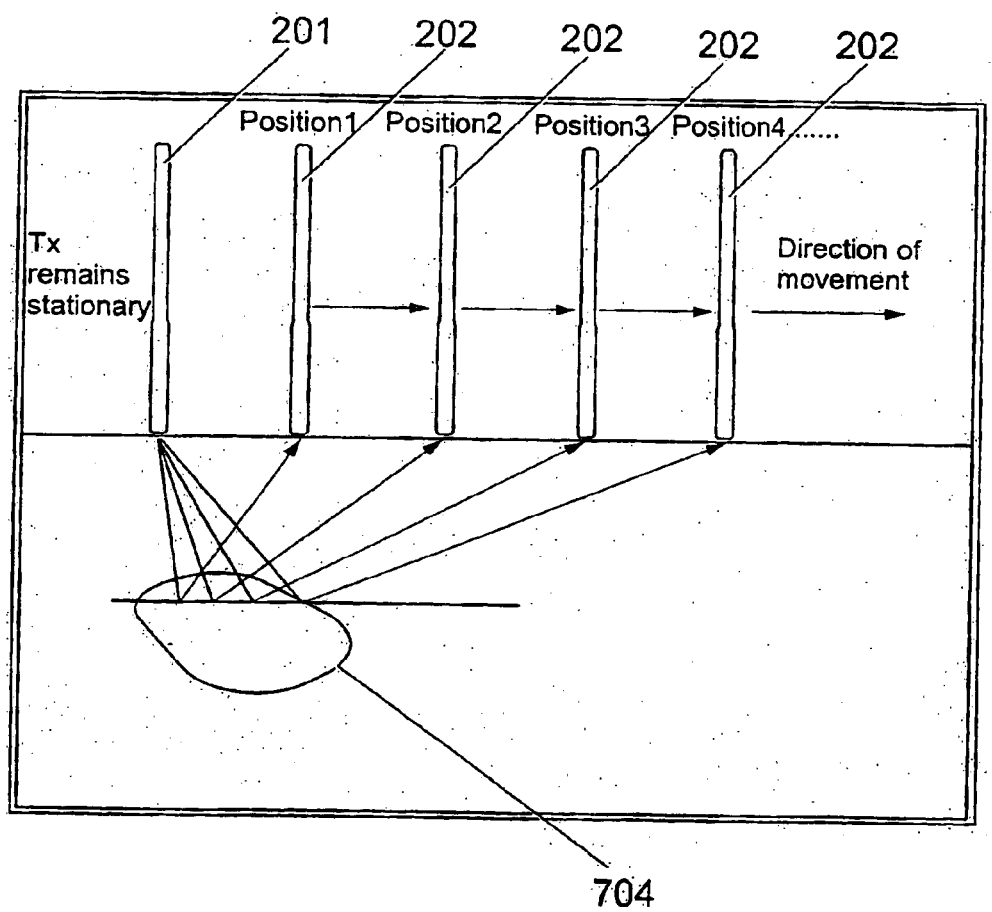
FIG. 11B illustrates the relative movement of a transmitting antenna and receiving antenna in accordance with a further embodiment of the invention.
Figure 13:
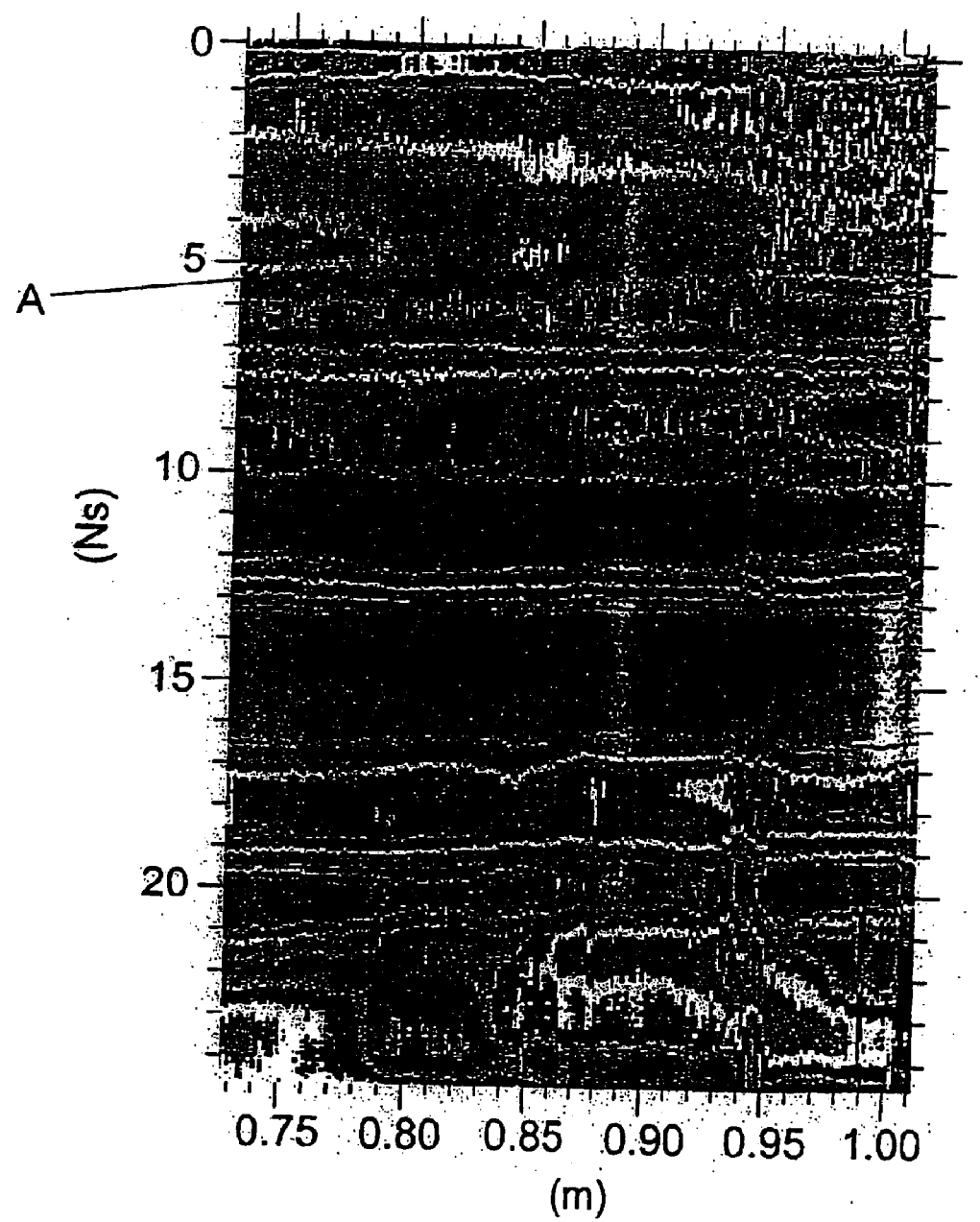
FIG. 13 is an image recorded using the radar apparatus according to the invention.

An example image obtained by means of the invention is shown in FIG. 11. The image represents a scan of a short cylindrical core of gold in a quartzite seam indicated at A. The width of this short scanned portion is 280 mm and the diameter of the gold core is approximately 40 mm.

The vertical dimension reflects the time domain and the horizontal scale has been rectified to represent the length of the core scanned by the moving antenna pair. The top of the image is 0 ns. Further time delays represent signals reflected from deeper within the sample core. Looking down through the core reflections are recorded to about 5.4 ns. Two further harmonic reflections are provided which provide information on surface roughness of the core and arise from too much initial power being used to generate the radar pulse. The first reflection lies from approximately 7 ns to 13 ns in time range and the second multiple surface reflection shows an enlarged portion of the core from 17 ns to 25 ns, the limit of the 25 ns time window selected.

The selection of appropriate circular slit apertures 224, 225 and ring spacings 226 and the choice of dielectric filler 228 which launches the wave enables the internal structure of the core to be perceived. If the anode length is proportional to the tube length as previously described, for example $1/\alpha$ or in this case 1/10th of the total internal telescope tube 227 length, then the time delay of the radar beam (i.e., the time from emission to detection) is multiplied by the reciprocal a of the fraction $1/\alpha$; i.e., the actual time delay $T_D = \alpha$ x the expected time delay $T_E$, where $T_E$ is as is given in conventional ground penetrating radar (GPR) formulae. Using the conventional GPR Range Formulae, this 40 mm, core of quartzite with a mean dielectric constant ($\epsilon_R = 5$) should have produced an equivalent time range length on the image of 0.54 ns, but the 10:1 factor stretched the time range because the beam was slowed down in the telescope and this resulted in a time range image spanning 5.4 ns. This is considered by the inventor to be a tube geometry and dielectric lens effect, and will assist in the near range focusing of radio-wave cameras and microscopes as well as radio-wave telescopes for mapping deep below ground level or the sea-bed.

The above description relates to particular embodiments of the invention. In general, the values or ranges of values indicated for various parameters may all vary and may be dependent on the particular application of the invention.

Furthermore, if the dielectric properties of the cladding material surrounding the antenna of the telescopes vary under given conditions, for example if the dielectric constant is thermally dependent, such as is the case with barium titanate, then it is possible to detect such conditions by using the invention to "stare" at the substance and monitoring the change in the received spectral data. This could enable the thermal conditions of subterranean structures/substances/objects to be determined. Other dielectrics of interest include lead zirconate titanate (PZT) and ammonium dihydrogen phosphate.

For the removal of doubt, wherever specific reference has been made to a "substance", "sample" or the like, the term may be taken to include other objects, liquids and powders as well as larger or smaller scale geological, marine or biological features etc. The term "subject" as used herein means any such substance, sample, object, feature etc. to be imaged, detected or analysed by means of the invention.

It will be understood that for certain applications of the invention, the transmitting and receiving antennas, antenna arrays or antenna assemblies may be combined in transceiver arrays or assemblies.

While several embodiments of the present invention have been described and illustrated, it will be apparent to those skilled in the art once given this disclosure that various modifications, changes, improvements and variations may be made without departing from the spirit or scope of this invention.

What is claimed is:

1. A radar antenna assembly for use as a transmitter, receiver or transceiver comprising:
    a tubular casing having a radar-reflective inner surface and having a first end, a second end and a longitudinal axis;
    a radar-reflective reflector closing said first end;
    an aperture disposed at said second end;
    focussing means at said second end;
    at least one elongate antenna element extending substantially parallel to said longitudinal axis from said reflector towards said second end; and
    dielectric material substantially filling the interior volume of said tubular casing.

2. A radar antenna assembly as claimed in claim 1, wherein said focussing means includes a plurality of concentric slit ring apertures located at said second end.

3. A radar antenna assembly as claimed in claim 1, wherein said focussing means includes at least one dielectric lens element located at said second end.

4. A radar antenna assembly as claimed in claim 3, wherein said dielectric lens element comprises a planar lens element.

5. A radar antenna assembly as claimed in claim 3, wherein said dielectric lens element comprises a planoconcave lens element.

6. A radar antenna assembly as claimed in claim 3, wherein said dielectric lens element comprises a planoconvex lens element.

7. A radar antenna assembly as claimed in claim 1, wherein said tubular casing has an inner diameter $D_T$ of which is an integer multiple of the diameter $D_A$ of said at least one antenna element.

8. A radar antenna assembly as claimed in claim 1, wherein said tubular casing has an interior length $L_T$ which is an integer multiple of the length $L_A$ of said at least one antenna element.

9. A radar antenna assembly as claimed in claim 1, wherein an interior surface of said tubular casing comprises an antenna cathode and said elongate antenna element comprises an antenna anode.

10. A radar antenna assembly as claimed in claim 9, wherein said elongate antenna element extends along said longitudinal axis.

11. A radar antenna assembly as claimed in claim 1, including at least two elongate antenna elements, at least one of which comprises an antenna cathode and at least one of which comprises an antenna anode.

12. A radar antenna assembly as claimed in claim 11, wherein said elongate antenna elements are disposed symmetrically about the longitudinal axis of the tubular casing.

13. A radar antenna assembly as claimed in claim 12, wherein said elongate antenna elements have substantially equal lengths and diameters.

14. A radar antenna assembly as claimed in claim 13, wherein the interior diameter $D_T$ of the tubular casing is an integer multiple of the diameter $D_A$ of said elongate antenna elements and of the spacing between adjacent pairs of said elongate antenna elements.

15. A radar antenna assembly as claimed in claim 1, wherein said dielectric material is a liquid.

16. A radar antenna assembly as claimed in claim 1, wherein said dielectric material is a solid.

17. A radar antenna assembly as claimed in claim 1, wherein said dielectric material is a powdered solid packed into the interior of said tubular casing.

18. A radar antenna assembly comprising a closed chamber adapted to contain a sample of material, said chamber including four substantially triangular side walls together defining an open-based pyramidal structure, said assembly including transmitter antenna elements disposed on interior surfaces of a first opposed pair of said triangular side walls and receiver antenna elements disposed on interior surfaces of a second opposed pair of said triangular side walls.

19. A radar antenna assembly as claimed in claim 18, wherein said antenna elements comprise bowtie dipole antennas with respective cathode and anode elements disposed on said opposed pairs of said triangular side walls.

20. A radar antenna apparatus as claimed in claim 18, wherein the base of said pyramidal structure is closed by a generally planar base wall, said chamber comprising the interior volume of said pyramidal structure.

21. A radar antenna assembly as claimed in claim 18, wherein said chamber comprises a closed volume communicating with the open base of said pyramidal structure.

22. A radar system comprising pulsed signal generating means, transmitter antenna means, receiver antenna means, control means for controlling the operation of said pulsed-signal generating means, analog-digital converter means for digitising signals received by said receiver antenna means, and data storage means for storing said digitised signals, wherein said transmitter antenna means and receiver antenna means comprise at least one radar antenna including one of:
- (i) a tubular casing having a radar-reflective inner surface and having a first end, a second end and a longitudinal axis;
  a radar-reflective reflector closing said first end;
  an aperture disposed at said second end;
  at least one elongate antenna element extending substantially parallel to said longitudinal axis from said reflector towards said second end; and
  dielectric material substantially filling the interior volume of said tubular casing; or
- (ii) a closed chamber adapted to contain a sample of material, said chamber including four substantially triangular side walls together defining an open-based pyramidal structure, said assembly including transmitter antenna elements disposed on interior surfaces of a first opposed pair of said triangular side walls and receiver antenna elements disposed on interior surfaces of a second opposed pair of said triangular side walls.

23. A radar system as claimed in claim 22, wherein said transmitter antenna means comprises at least one transmitter radar antenna assembly and said receiver antenna means comprises at least one receiver radar antenna assembly said transmitter antenna assembly and said receiver antenna assembly each comprising:
a tubular casing having a radar-reflective inner surface and having a first end, a second end and a longitudinal axis;
a radar-reflective reflector closing said first end;
an aperture disposed at said second end;
at least one elongate antenna element extending substantially parallel to said longitudinal axis from said reflector towards said second end; and dielectric material substantially filling the interior volume of said tubular casing.

24. A radar system as claimed in claim 23, wherein said transmitter and receiver antenna assemblies are disposed so as to transilluminate a subject.

25. A radar system as claimed in claim 23, wherein said transmitter and receiver antenna assemblies are disposed so as to be co-axially aligned on opposite sides of a subject.

26. A radar system as claimed in claim 23, wherein said transmitter and receiver antenna assemblies are connected to a closed sample chamber adapted to enclose a subject.

27. A radar system as claimed in claim 23, wherein said transmitter and receiver antenna assemblies are disposed such that said receiver antenna assembly receives a signal transmitted by said transmitter antenna assembly and reflected from a subject.

28. A radar system as claimed in claim 27, wherein said transmitter and receiver antenna assemblies are arranged such that their longitudinal axes are substantially parallel to one another with their second ends facing in the same direction.

29. A radar system as claimed in claim 27, wherein said system is adapted to be portable.

30. A radar system as claimed in claim 27, wherein said system is adapted to be carried by a land vehicle.

31. A radar system as claimed in claim 27, wherein said system is adapted to be carried by a water-borne vessel.

32. A radar system as claimed in claim 27, wherein said system is adapted to be carried by a submersible vehicle.

33. A radar system as claimed in claim 27, wherein said system is adapted to be carried by an airborne vehicle.

34. A radar system as claimed in claim 27, wherein said system is adapted to be carried by a space vehicle.

35. A radar system as claimed in claim 27, wherein the position of said transmitter antenna assembly is fixed relative to said receiver antenna assembly.

36. A radar system as claimed in claim 27, wherein at least one of said transmitter antenna assembly and said second antenna assembly is adapted to be movable relative to a subject.

37. A radar system as claimed in claim 27 in which one of said transmitter and receiver antenna assemblies is adapted to be movable relative to the other.

38. A radar system as claimed in claim 27, including a plurality of transmitter antenna assemblies.

39. A radar system as claimed in claim 27, including a plurality of receiver antenna assemblies.

40. A radar system as claimed in claim 27, for use with close range subjects, in which said control means is adapted to control said pulsed signal generating means so as to generate pulses with a pulse repetition frequency of the order of 100 kHz.

41. A radar system as claimed in claim 27, for use with close range subjects, in which said control means is adapted to control said pulsed signal generating means so as to generate pulses with a pulse width in the range 0.01 to 0.1 nanoseconds.

42. A radar system as claimed in claim 27, for use with close range subjects, adapted to capture data in a time range of 2 to 25 nanoseconds.

43. A radar system as claimed in claim 27, for use with close range subjects, adapted to transmit pulses with a minimum frequency in the range 100 to 1000 MHz and with a maximum frequency in the range 1000 to 10000 MHz.

44. A radar system as claimed in claim 27, for use with close to medium range subjects, in which said control means is adapted to control said pulsed signal generating means so as to generate pulses with a pulse repetition frequency of the order of 25 to 100 kHz.

45. A radar system as claimed in claim 27, for use with close to medium range subjects, in which said control means is adapted to control said pulsed signal generating means so as to generate pulses with a pulse width in the range 1 to 10 nanoseconds.

46. A radar system as claimed in claim 27, for use with close to medium range subjects, adapted to capture data in a time range of 2000 to 10000 nanoseconds.

47. A radar system as claimed in claim 27, for use with close to medium range subjects, adapted to transmit pulses with a minimum frequency in the range 12.5 to 125 MHz and with a maximum frequency in the range 200 to 2000 MHz.

48. A radar system as claimed in claim 27, for use with long range subjects, in which said control means is adapted to control said pulsed signal generating means so as to generate pulses with a pulse repetition frequency of the order of 3.125 to 50 kHz.

49. A radar system as claimed in claim 27, for use with long range subjects, in which said control means is adapted to control said pulsed signal generating means so as to generate pulses with a pulse width in the range 10 to 25 nanoseconds.

50. A radar system as claimed in claim 27, for use with long range subjects, adapted to capture data in a time range of 20000 to 250000 nanoseconds.

51. A radar system as claimed in claim 27, for use with long range subjects, adapted to transmit pulses with a minimum frequency in the range 1 to 12.5 MHz and with a maximum frequency in the range 12.5 to 200 MHz.

52. A radar system as claimed in claim 27, further including data processing means for processing said digitised signals.

53. A radar system as claimed in claim 52, wherein said data processing means is adapted to process said digitised signals for the purposes of at least one of imaging, measuring, mapping, detecting, identifying and typecasting said subject.

54. A radar system as claimed in claim 22,
wherein said transmitter antenna means comprises at least one transmitter radar antenna assembly and said receiver antenna means comprises at least one receiver radar antenna assembly, said transmitter antenna assembly and said receiver antenna assembly disposed such that said receiver antenna assembly receives a signal transmitted by said transmitter antenna assembly and reflected from a subject, said transmitter antenna assembly and said receiver antenna assembly each comprising:

a tubular casing having a radar-reflective inner surface and having a first end, a second end and a longitudinal axis;

a radar-reflective reflector closing said first end;

an aperture disposed at said second end;

at least one elongate antenna element extending substantially parallel to said longitudinal axis from said reflector towards said second end: and dielectric material substantially filling the interior volume of said tubular casing.

the system farther including data processing means for processing said digitised signals, wherein said data processing means is adapted to typecast a subject by: irradiating the subject with a pulsed, broad band radar frequency signal transmitted by at least one transmitter antenna; detecting a return signal following interaction of said transmitted signal with said subject, using at least one receiver antenna; calculating an energy/frequency spectrum of said return signal; and analysing said energy/frequency spectrum to obtain a characteristic energy/frequency signature of said subject.

55. A method of typecasting a subject comprising the steps of: irradiating the subject with a pulsed, broad band radar frequency signal transmitted by at least one transmitter antenna; detecting a return signal following interaction of said transmitted signal with said subject, using at least one receiver antenna; calculating an energy/-frequency spectrum of said return signal; and analysing said energy/-frequency spectrum to obtain a characteristic energy/-frequency signature of said subject.

56. A method as claimed in claim 55, wherein said step of analysing said energy/-frequency spectrum comprises performing a statistical analysis of said energy/-frequency spectrum.

57. A method as claimed in claim 56, wherein said statistical analysis includes at least one of principal components analysis, maximum likelihood classification and multivariate classification.

58. A method as claimed in claim 55, wherein said step of analysing said energy/-frequency spectrum comprises frequency classification using energy bins.

59. A method as claimed in claim 55, wherein said step of analysing said energy/frequency spectrum comprises energy classification using frequency bins.

60. A method of identifying an unknown subject comprising the steps of:
obtaining an energy/-frequency signature of said subject by irradiating the subject with a pulsed, broad band radar frequency signal transmitted by at least one transmitter antenna, detecting a return signal following interaction of said transmitted signal with said subject, using at least one receiver antenna; calculating an energy/frequency spectrum of said return signal; and analysing said energy/frequency spectrum to obtain a characteristic energy/frequency signature of said subject; and comparing said energy/-frequency signature of the unknown subject to a database of energy/-frequency signatures of known subjects.

61. A method of typecasting a subject comprising the steps of: irradiating the subject with a pulsed, broad band radar frequency signal transmitted by at least one transmitter antenna; detecting a return signal following interaction of said transmitted signal with said subject, using at least one receiver antenna; calculating an energy/frequency spectrum of said return signal; and analysing said energy/frequency spectrum to obtain a characteristic energy/frequency signature of said subject, wherein the method is implemented using a radar system comprising pulsed signal generating means, transmitter antenna means, receiver antenna means, control means for controlling the operation of said pulsed signal generating means, analog-digital converter means for digitising signals received by said receiver antenna means, data processing means for processing said digitised signals, and data storage means for storing said digitised signals, wherein said transmitter antenna means and receiver antenna means comprise at least one radar antenna including one of:

(i) a tubular casing having a radar-reflective inner surface and having a first end, a second end and a longitudinal axis;

a radar-reflective reflector closing said first end;

an aperture disposed at said second end;

at least one elongate antenna element extending substantially parallel to said longitudinal axis from said reflector towards said second end; and dielectric material substantially filling the interior volume of said tubular casing; or (ii) a closed chamber adapted to contain a sample of material, said chamber including four substantially triangular side walls together defining an open-based pyramidal structure, said assembly including transmitter antenna elements disposed on interior surfaces of a first opposed pair of said triangular side walls and receiver antenna elements disposed on interior surfaces of a second opposed pair of said triangular side walls said transmitter antenna means comprises at least one transmitter radar antenna assembly and said receiver antenna means comprises at least one receiver radar antenna assembly said transmitter antenna assembly and said receiver antenna assembly disposed such that said receiver antenna assembly receives a signal transmitted by said transmitter antenna assembly and reflected from a subject, said transmitter antenna assembly and said receiver antenna assembly each comprising:

a tubular casing having a radar-reflective inner surface and having a first end, a second end and a longitudinal axis;

a radar-reflective reflector closing said first end;

an aperture disposed at said second end;

at least one elongate antenna element extending substantially parallel to said longitudinal axis from said reflector towards said second end: and dielectric material substantially filling the interior volume of said tubular casing.

* * * * *